(12) United States Patent
Bhalgat et al.

(10) Patent No.: US 6,316,267 B1
(45) Date of Patent: Nov. 13, 2001

(54) LUMINESCENT PROTEIN STAINS AN THEIR METHOD OF USE

(75) Inventors: Mahesh K. Bhalgat, Saint Louis County, MO (US); Zhenjun Diwu, Lane County, OR (US); Richard P. Haugland, Lane County, OR (US); Wayne F. Patton, Lane County, OR (US)

(73) Assignee: Molecular Probes, Inc., Eugene, OK (US)

( * ) Notice: Subject to any disclaimer, the term of this patent is extended or adjusted under 35 U.S.C. 154(b) by 0 days.

(21) Appl. No.: 09/429,739

(22) Filed: Oct. 27, 1999

Related U.S. Application Data
(60) Provisional application No. 60/105,839, filed on Oct. 27, 1998, provisional application No. 60/113,828, filed on Dec. 23, 1998, and provisional application No. 60/126,346, filed on Mar. 26, 1999.

(51) Int. Cl.[7] .................... G01N 33/48; G01N 33/52; G01N 33/68
(52) U.S. Cl. .................. 436/86; 436/87; 436/88; 436/164; 436/172; 436/175; 436/177; 422/61
(58) Field of Search .................. 436/86–88, 164, 436/172, 175, 177; 422/61

(56) References Cited

U.S. PATENT DOCUMENTS

| | | | |
|---|---|---|---|
| 5,316,906 | 5/1994 | Haugland et al. . | |
| 5,321,130 | 6/1994 | Yue et al. . | |
| 5,410,030 | 4/1995 | Yue et al. . | |
| 5,453,356 | * 9/1995 | Bard et al. ................ | 435/6 |
| 5,616,502 | 4/1997 | Haugland et al. . | |
| 5,731,147 | 3/1998 | Bard et al. . | |
| 6,140,138 | * 10/2000 | Bard et al. ................ | 436/537 |

FOREIGN PATENT DOCUMENTS

| | | |
|---|---|---|
| WO 93/06482 | 4/1993 | (WO) . |
| WO 94/24213 | 10/1994 | (WO) . |
| WO 97/20213 | 6/1997 | (WO) . |

OTHER PUBLICATIONS

Anderson et al., J. Chem. Soc. Dalton Trans. 2247 (1985).
Castellano et al. Analytical Biochemistry 255, 165 (1998).
Castellano et al. Photochemistry and Photobiology 67(2), 179 (1998).
Lim, et al., Anal. Bioch. 245, 184–195 (1997).
McWhinnie et al., Adv. Inorg. Chem. Radiochem. 12, 135 (1969).
Moucheron et al., J. Am. Chem. Soc. 118, 12834 (1996).
Patton et al., Methods in Molecular Biology, 112, 331 (1999).
Schwartz et al. J. Photochem Photobiol 112, 47 (1998).
Skotty et al. Journal of Chromatography B, 665, 27 (1995).
Szmacinski et al. Biochimica Et Biophysica Acta 1383, 151 (1998).
Terpetschnig et al. Analytical Biochemistry 251, 241 (1997).

* cited by examiner

*Primary Examiner*—Jeffrey Snay
(74) *Attorney, Agent, or Firm*—Anton Skaugset; Allegra Helfenstein

(57) ABSTRACT

The invention relates to the staining of poly(amino acids), including peptides, polypeptides and proteins in gels and on solid supports, using neutral or anionic complexes of transition metals.

36 Claims, 4 Drawing Sheets

LUMINESCENT PROTEIN STAINS AN THEIR METHOD OF USE

This application claims the priority of provisional application Ser. No. 60/105,839, filed Oct. 27, 1998; provisional application Ser. No. 60/113,828, filed Dec. 23, 1998; and provisional application Ser. No. 60/126,346, filed Mar. 26, 1999, all incorporated by reference.

FIELD OF THE INVENTION

The invention relates to the staining of poly(amino acids), including peptides, polypeptides and proteins in gels and on solid supports, using neutral or anionic complexes of transition metals.

BACKGROUND

Poly(amino acids), including peptides and proteins, are typically detected and characterized using gel electrophoresis, by solution quantitation assays or by detection on solid supports, such as filter membranes. Small amounts of protein or other poly(amino acids) are generally not visible to the naked eye, and must be stained before they can be localized and identified.

Two of the most common methods of staining poly(amino acids) in gels are COOMASSIE Brilliant Blue (CBB) staining and silver staining. For particular poly(amino acids), silver staining is approximately 100- to 1000-fold more sensitive than CBB staining, but both methods have disadvantages. The use of luminescent reagents for protein detection offers the possibility of greatly enhanced sensitivity and increased linear quantitation range, while simultaneously increasing the ease of use of the staining reagent. By "luminescent" is meant any reagent that is fluorescent, phosphorescent or chemiluminescent.

The use of selected styryl and merocyanine dyes as fluorescent stains for poly(amino acids) in gels (e.g. SYPRO® Red and SYPRO® Orange dyes of Molecular Probes, Inc.), on membranes or other supports, and in solution (U.S. Pat. No. 5,616,502 to Haugland et al., hereby incorporated by reference) is very rapid, relatively insensitive to poly(amino acid) composition, does not require destaining, and is more than an order of magnitude more sensitive than CBB staining.

Unfortunately, organic fluorescent dyes typically suffer from the drawback of high background noise. Europium complexes of sulfonated bathophenanthroline that permit "time-resolved" detection reduce the interference from background noise (see M. J. Lim, et al., ANAL. BIOCH. 245, 184–195 (1997), and International Publication No. WO 97/20213). However, the europium complexes are not readily excited by visible light, and require ultraviolet illumination for optimal luminescence, thus they cannot be used with commercially available laser-excited gel scanners. In addition, the europium complexes bind to proteins reversibly, and decompose at low concentrations.

Some dyes have been used to stain proteins using so-called "colloidal" dye formulations. A restricted number of sulfonated triphenylmethane dyes are known to form colloidal protein-dye complexes. Other sulfonated dyes do not selectively stain proteins in polyacrylamide gels when prepared in such formulations.

The transition metal complexes used to practice the method of the instant invention have an overall charge that is neutral, or that is anionic. The complexes are highly stable, even in dilute solution, associate strongly with proteins in solution, on membranes, in biological cells, and in electrophoretic gels, yielding bright, long-lifetime, visible luminescence. The instant metal complexes bind strongly and noncovalently to proteins, even in neutral or basic pH solutions, and provide higher sensitivity poly(amino acid) detection than any of the methods described above, and can be used with both ultraviolet and with visible light excitation.

SUMMARY OF THE INVENTION AND DESCRIPTION OF THE PREFERRED EMBODIMENTS

Figure 1:
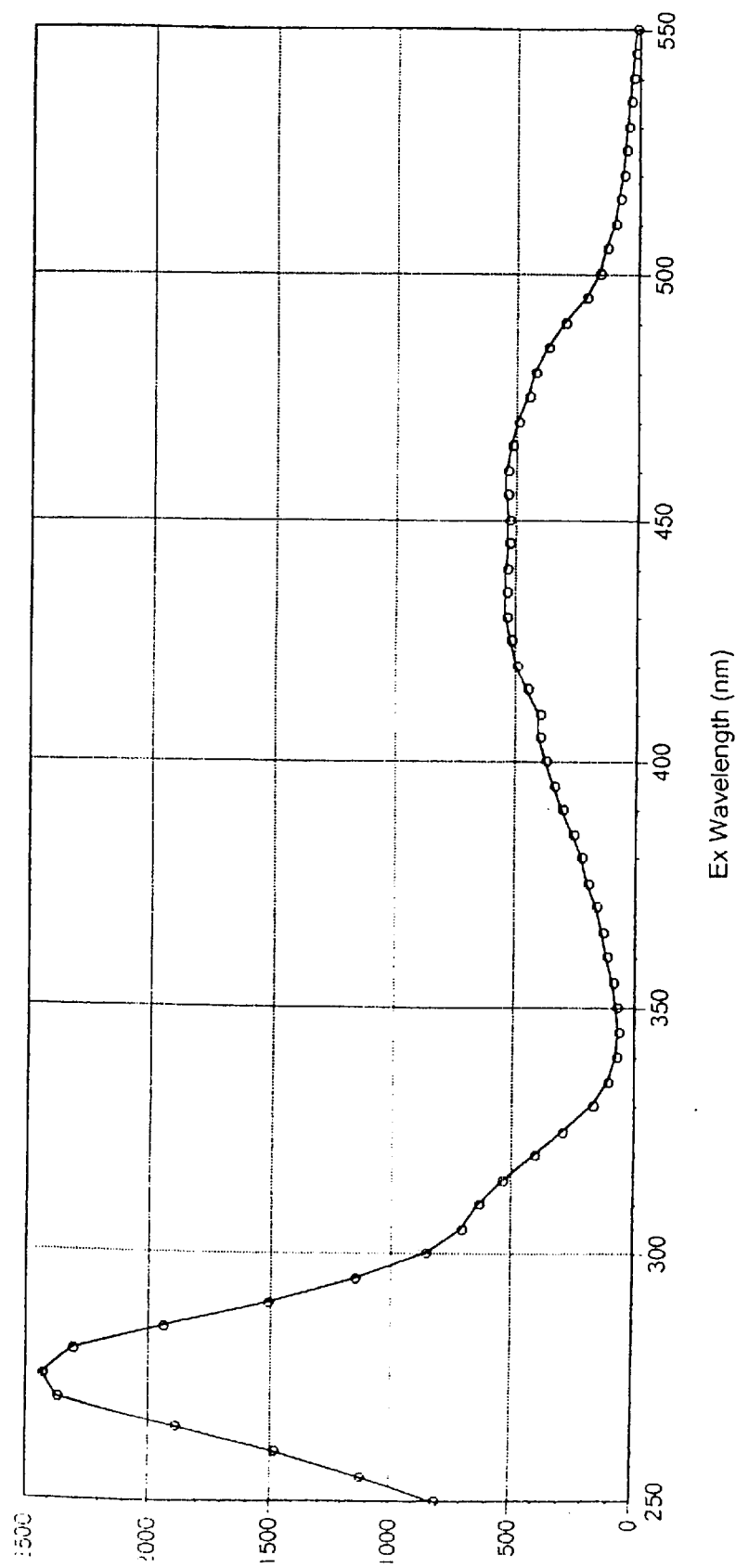
FIG. 1: Excitation spectra of a 10 $\mu$M aqueous solution of Compound 1,150 $\mu$M citric acid.
Figure 2:
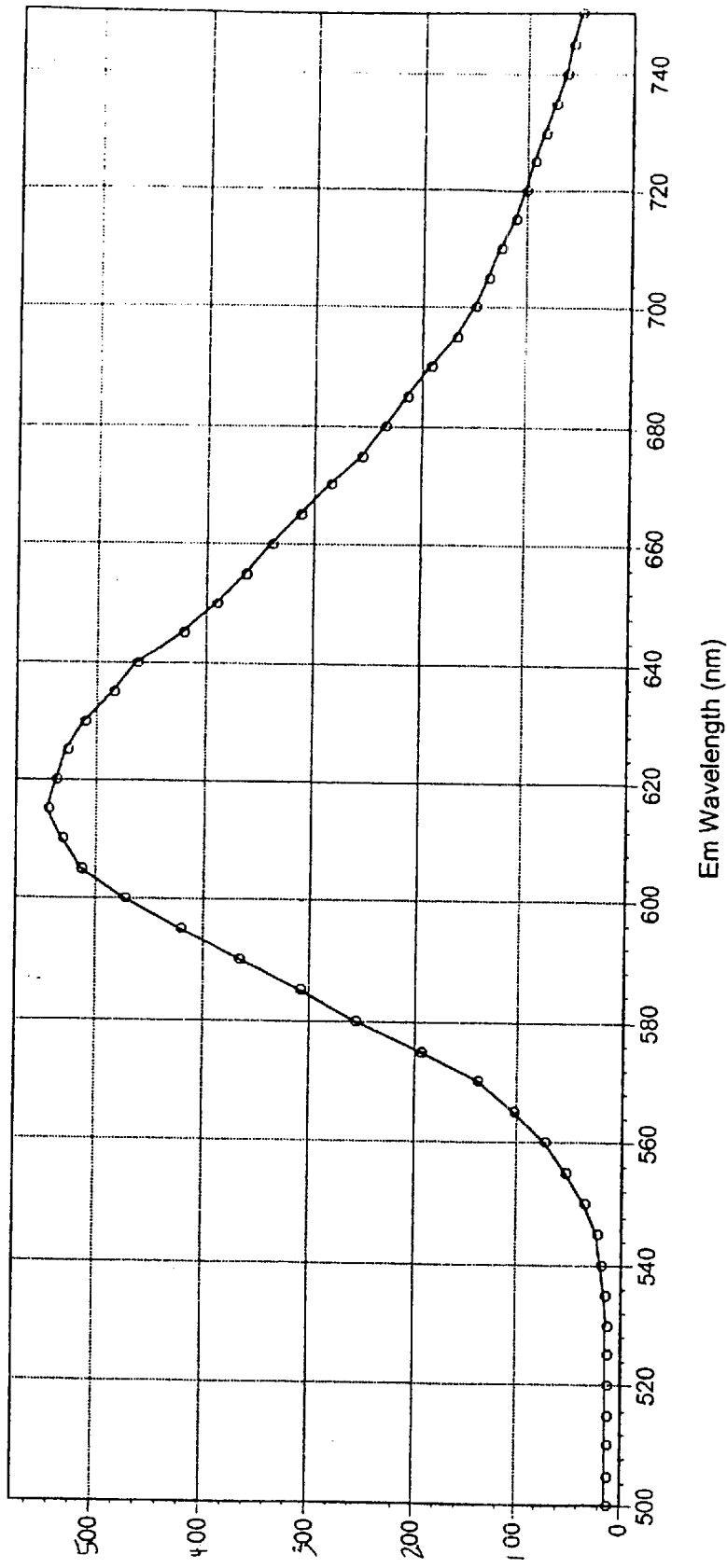
FIG. 2: Emission spectra of a 10 $\mu$M aqueous solution of Compound 1,150 $\mu$M citric acid, after excitation at 440 nm.
Figure 3:
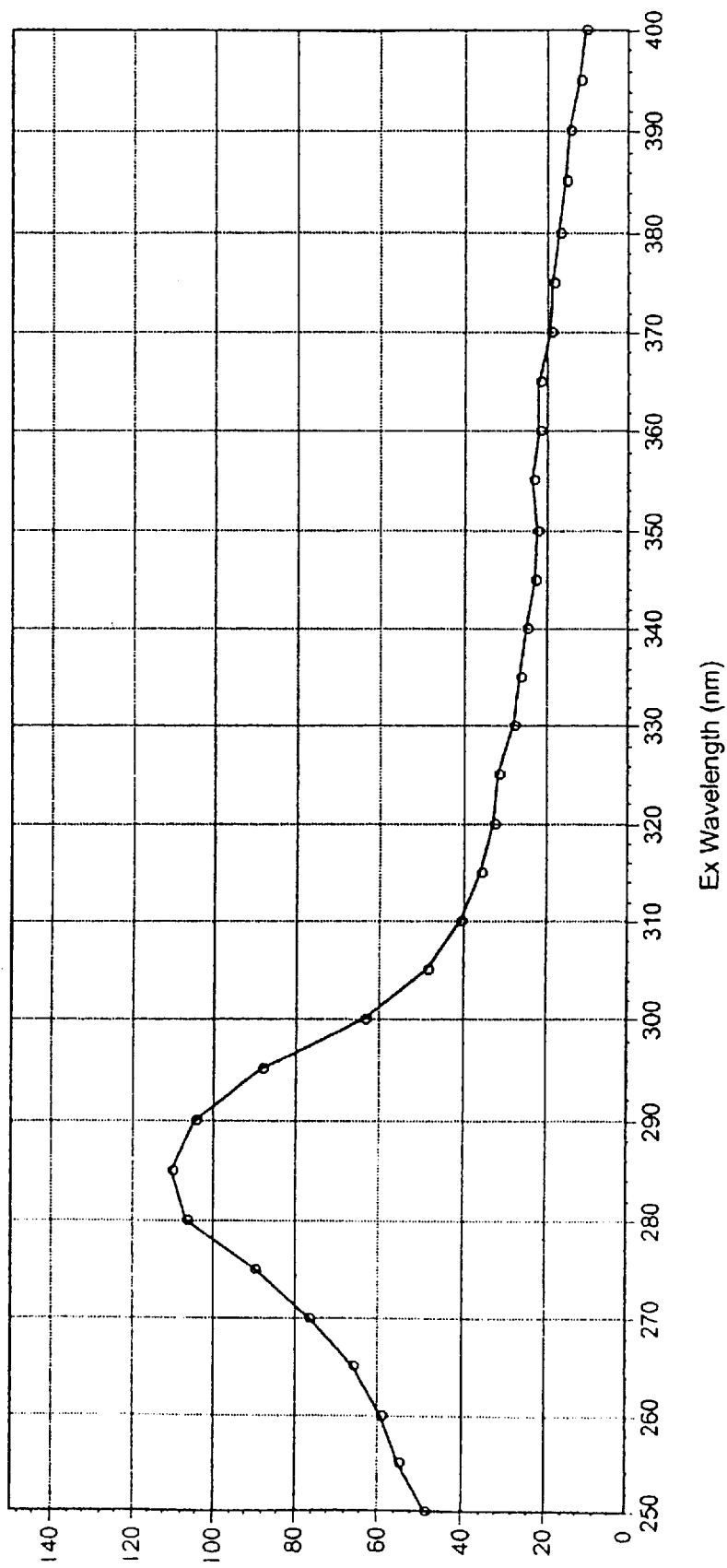
FIG. 3: Excitation spectra of a 10 $\mu$M aqueous solution of Compound 3.
Figure 4:
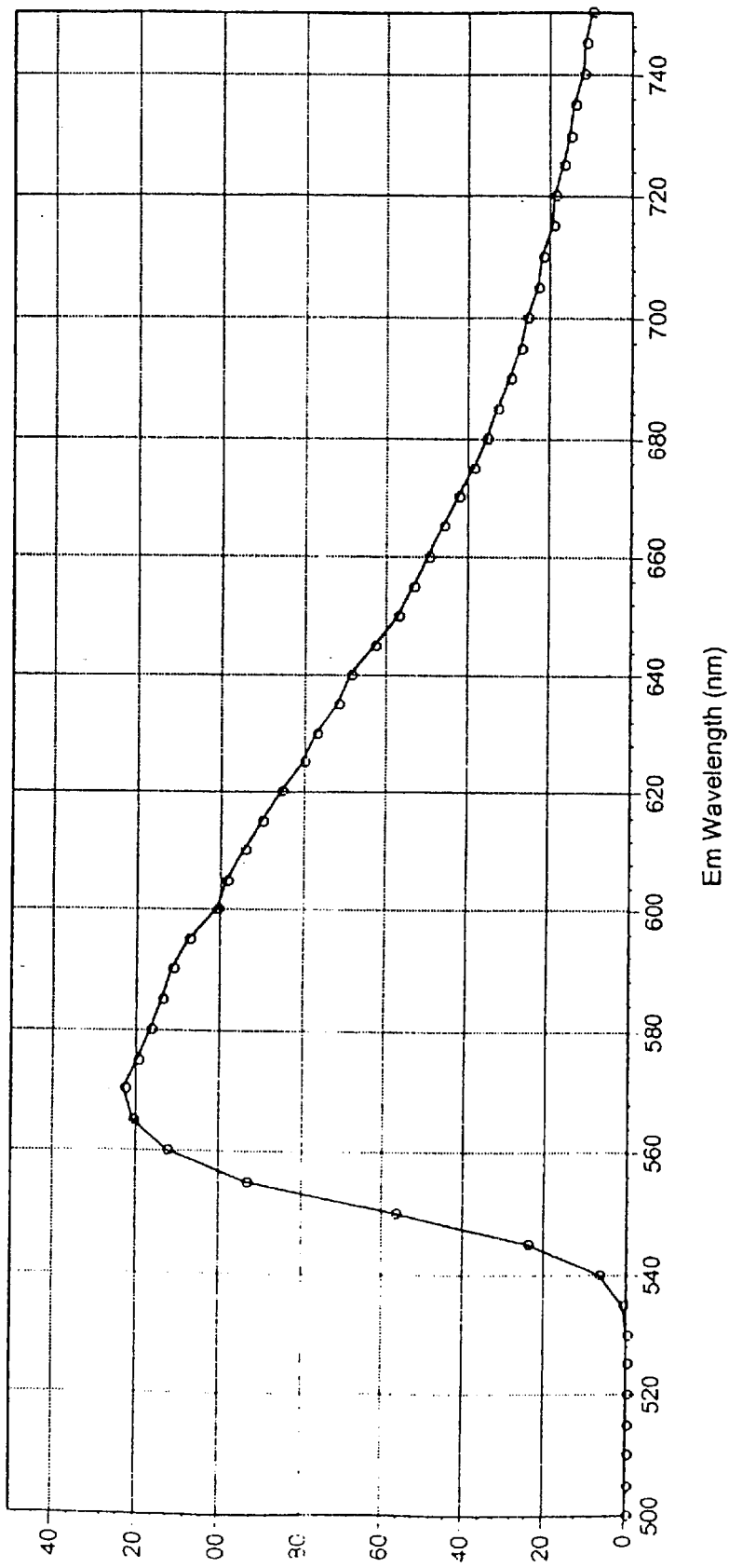
FIG. 4: Emission spectra of a 10 $\mu$M aqueous solution of Compound 3, after excitation at 385 nm.

The invention relates to the staining of poly(amino acids) by metal ligand complexes. One aspect of the invention is novel staining mixtures comprising a metal atom coordinated with a plurality of ligands. Another aspect of the invention is the use of the selected metal ligand complexes for staining poly(amino acids). Yet another aspect of the invention is distinguishing cells based on staining with the selected metal ligand complexes.

The Metal Complex

The method of the invention utilizes a staining mixture that comprises one or more metal ligand complexes. The metal ion is typically a transition metal of Group 7, Group 8, Group 9, or Group 10 having an atomic number greater than 42, where the transition metal has any electronic configuration that is compatible with binding nitrogen donor ligands. In one embodiment, the metal ion has a $d^6$ electron configuration, such as a rhenium (I), ruthenium (II), osmium (II), rhodium (III), or an iridium (III) ion. In another embodiment, the metal ion has a $d^8$ electronic configuration, such as a platinum (II) ion.

In one aspect of the invention, the metal ion is ruthenium (II), osmium (II), rhenium (I), or platinum (II). In another aspect, the metal ion is ruthenium (II) or rhenium (I). In yet another aspect, the metal ion is ruthenium (II).

In some embodiments, the transition metal is an unstable isotope that is naturally radioactive such as $Ru^{103}$, $Ru^{106}$ or $Tc^{99}$. Where the metal complex of the invention is radioactive, the complex is useful for detection of proteins by either its luminescence, by radiography, or both.

The ligands of the invention occupy the coordination sphere of the transition metal, and are mono- or polydentate nitrogen donor ligands, wherein at least one of the ligands is further substituted by an anionic moiety. A ligand that is a nitrogen donor is an organic moiety that binds to transition metals via the donation of 2 electrons from the lone pair on a nitrogen atom. In the instant ligands, the nitrogen atom is typically incorporated into a heteroaromatic ring. Where the ligand possesses a single nitrogen atom for binding to the metal ion, it is a monodentate ligand. Where it possesses two nitrogen atoms for binding, it is a bidentate ligand. Where it possesses three nitrogen atoms for binding, it is a tridentate ligand, and so on. Typically, the nitrogen donor ligands of the invention are bidentate or tridentate, more preferably bidentate.

The metal complexes of the invention contain one or more metal ions. In one aspect, the metal ion exhibits an octahedral or square planar coordination geometry. Where the metal ion has an octahedral geometry, the nitrogen atoms of the donor ligands are oriented around the metal ion at the vertices of an octahedron, with the metal ion at the center of the octahedron. Such metal ions of the invention may bind 1–6 ligands, which may be the same or different. For example, as shown below, a metal ion may bind six monodentate ligands, three bidentate ligands, or two tridentate ligands. The metal ion may even bind a single hexadentate ligand. Alternatively the metal complex possesses a mixture of distinct ligands.

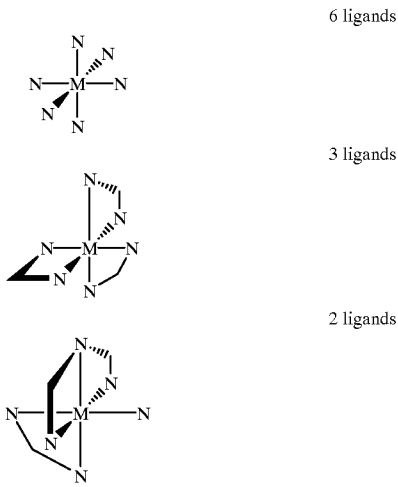

Where the metal complexes of the invention are square planar, the nitrogen atoms of the donor ligands are oriented at the vertices of a square plane, with the metal ion at the center of the square. Such metal ions may bind four monodentate ligands, or two bidentate ligands, as shown below:

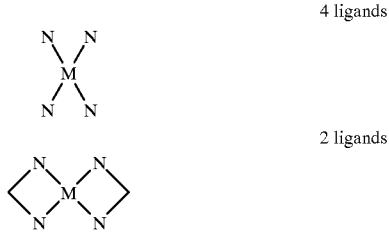

Although the geometry of a given metal center of the invention exists in three dimensions, the complexes of the invention are depicted in two dimensions for ease of presentation. As is well known for octahedral metal complexes, for example, the complex may exist as a single stereoisomer or a mixture of stereoisomers. The absolute configuration of ligands around the metal ion does not appear to influence the ability of the complex to stain poly(amino acids).

A given metal complex optionally contains multiple ligands of the same chemical formula, or contains more than one structurally distinct type of ligand, such as a complex that contains a bidentate ligand in combination with four monodentate ligands, a tridentate ligand in combination with a bidentate and monodentate ligand, or a combination of three distinct bidentate ligands. The metal complex of the invention optionally incorporates ligands substituted by one or more anionic moieties, and ligands that are not substituted by anionic moieties. The ligands of the invention optionally simultaneously bind to two or more metal ions and act as bridging ligands. This is particularly accomplished by utilizing a nitrogen donor ligand that accommodates more than one metal binding site (for example, Compound 5). Where the metal complex incorporates more than one metal ion, each metal ion optionally has the same or different coordination geometry.

The ligands of the instant invention are aromatic nitrogen donor ligands, and comprise at least one heteroaromatic ring containing a nitrogen atom, through which the ligand binds to the metal atom or ion of the invention. In one embodiment, the ligand comprises two heteroaromatic rings that are linked by a single covalent bond, or by an appropriate covalent linkage. In another embodiment, the ligand comprises two heteroaromatic rings that are linked by an additional fused aromatic ring. In yet another embodiment, the ligand comprises three heteroaromatic rings, that are joined by a single covalent bond, or by an appropriate covalent linkage. In any embodiment, the heteroaromatic rings of the ligand are optionally substituted, and optionally incorporate one or more additional heteroatoms that are N, O, or S. Where the ligands of the invention incorporate multiple heteroaromatic rings, they are typically polydentate, and bind to the same or different metal centers via the heteroaromatic ring nitrogen atoms.

The ligands of the invention are optionally substituted by a wide variety of substituents, including alkyl, aryl, and heteroaryl substituents, alkenes, alkynes, halogens, ethers, thioethers, amides, esters, acids, and nitrogen containing groups. In one embodiment, the ligand substituents are simple substituents such as H, halogen, or CN. In another embodiment, allowed substituents include alkyl, perfluoroalkyl, or alkoxy having 1–6 carbon atoms; carboxy (—COOH), carboxyalkyl, carboxyalkoxy, carboxyalkylamino, or carboxylalkylthio, each having 2–7 carbon atoms. Other ligand substituents are optionally amino, salt of amino (where the counterion is a halide, sulfate, sulfonate, substituted sulfonate, phosphate, perchlorate, tetrafluoroborate, tetraphenylboride, or an anion of an aromatic or aliphatic carboxylic acid), alkylamino or dialkylamino, where each alkyl group has 1–6 carbon atoms. Still other ligand substituents are optionally aryl or heteroaryl. Alternatively, two or more ligand substituents taken in combination form additional fused rings that are themselves optionally substituted by the substituents described above.

An aryl substituent, as used herein, is a six-membered aromatic ring, attached by a single covalent bond, which is typically phenyl or substituted phenyl, but also encompasses simple aromatic substituents such as naphthyls and substituted naphthyls.

Heteroaryl, as used herein, is an aromatic group that contains at least one heteroatom (a non-carbon atom forming part of the ring structure). A heteroaryl substituent is optionally a 5- or 6-membered ring, or is part of a fused 2- or 3-ring structure. A heteroaryl substituent optionally contains one or more heteroatoms, e.g. pyrrolyl, pyridyl, thienyl, or furanyl (single ring, single heteroatom), or oxazolyl, isoxazolyl, oxadiazolyl, or imidazolyl (single ring, multiple heteroatoms), or benzoxazolyl, benzothiazolyl, or benzimidazolyl, (multi-ring, multiple heteroatoms), or quinolyl, benzofuranyl or indolyl (multi-ring, single heteroatom). Preferred heteroaryl substituents are pyridyl or quinolyl.

Aryl and heteroaryl substituents are typically used to modify the spectral properties, affinity, selectivity, solubility or reactivity of the resulting metal complex, or any combination of these factors. Both aryl and heteroaryl substituents of the instant ligands are independently and optionally substituted as described above for the heteroaromatic rings of the ligands of the invention, including halogen; sulfonic acid or salt of sulfonic acid; phosphonate; phosphate; boronate; alkyl, perfluoroalkyl or alkoxy (each having 1–6 carbon atoms); or carboxy, carboxyalkyl, carboxyalkoxy, carboxyalkylamino, or carboxyalkylthio (having 2–7 carbon atoms).

Additional selected ring substituents may also be utilized to alter the solubility of the resulting metal complex in either aqueous or organic solvents, to modify the spectral or protein-binding properties of the metal complex, or to modify the electronic environment of the metal center. Typically, the greater the degree of sulfonation on the ligand, the greater the degree of aqueous solubility the resulting metal complex possesses. The additional substitution of ammonium salts, carboxy, carboxyalkyl, carboxyalkoxy, carboxyalkylamino, or carboxyalkylthio or other highly polar substituents also results in enhanced aqueous solubility, improved protein binding or other desirable features.

For all embodiments of the invention, the metal complexes must possess at least one ligand that is itself substituted directly or indirectly by at least one anionic moiety. Anionic moieties are functional groups that possess a negative ionic charge at the pH ranges typically used when practicing the instant method. Anionic moieties include, without limitation, phosphate, thiophosphate, phosphonate, carboxylate, boronate, sulfate, sulfonate, thiosulfate, and thiosulfonate. Typically, at least one ligand is substituted by at least one sulfonate moiety. By sulfonate moiety is meant sulfonic acid (—$SO_3H$), sulfonate ion (—$SO_3^-$), or salt of sulfonate ion (—$SO_3X$, where X is typically an alkali metal cation or an ammonium cation). Typically, the charge of the sulfonate group is balanced by the charge of a cationic counterion. Alternatively, the charge of the sulfonate group is balanced by a charge formally present on the metal ion itself. At physiological or lower pH, sulfonate moieties are typically present as the sulfonate ion. Where the metal complexes of the invention are sulfonated, the complex itself is typically neutral or anionic in overall charge (in the absence of other ionizable groups on the complex). By overall charge is meant the electronic charge present on the complex of the metal ion with its associated ligands. It is understood in the art that where the overall charge negative, it is necessarily balanced by one or more cationic counterions. For example, a complex of ruthenium (II) that comprises a total of four sulfonate moieties on all of the ligands in the complex will have an overall charge of 2–. A complex of ruthenium (II) that comprises a total of six sulfonate moieties on all of the ligands in the complex will have an overall charge of 4–. The sulfonate groups present on the ligands of the invention may be bound directly to an aromatic nitrogen heterocycle, or be bound via a ring substituent, such as a sulfophenyl substituent or a sulfoalkyl substituent. The location of sulfonic acid substitution on the ligand is apparently not critical to the staining efficacy of the resulting metal complex, and complexes that incorporate mixtures of ligand isomers typically function as well as isomer-free complexes in practicing the method of the instant invention.

Useful nitrogen donor ligands of the invention include, without limitation pyridines, bipyridines, ter-pyridines, phenanthrolines, bathophenanthrolines, imidazoles, pyrroles, pyrazoles, indazoles, triazoles, pyrazines, pyrimidines, pyridazines, purines, porphyrins, phthalocyanines. In one aspect of the invention, the nitrogen donor ligands are bipyridines, ter-pyridines, phenanthrolines, and bathophenanthrolines. In another aspect of the invention, the nitrogen donor ligands are phenanthrolines and bathophenanthrolines. Nitrogen containing rings may also be further modified, such as by fusion to aromatic rings, for example to yield a benzotriazole or a biquinoline.

In one embodiment, the ligands of the invention possess at least two pyridyl rings, according to the general formula

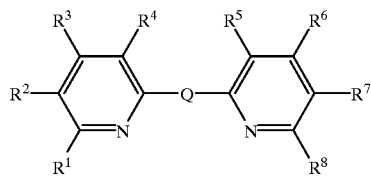

where the pyridyl rings have the primary ring substituents $R^1$, $R^2$, $R^3$, $R^4$, $R^5$, $R^6$, $R^7$, and $R^8$ that are independently selected from H, halogen, CN, alkyl, perfluoroalkyl, or alkoxy having 1–6 carbon atoms; carboxy (—COOH), carboxyalkyl, carboxyalkoxy, carboxyalkylamino, carboxylalkylthio, each having 2–7 carbon atoms, amino, salt of amino (where the counterion is a halide, sulfate, sulfonate, phosphate, perchlorate, tetrafluoroborate, tetraphenylboride, or an anion of an aromatic or aliphatic carboxylic acid), alkylamino or dialkylamino, where each alkyl group has 1–6 carbon atoms. Where the ligand is sulfonated, at least one substituent is sulfonic acid, or salt of sulfonic acid. Still other ring substituents are optionally aryl or heteroaryl. Typically, the ligand has no more than two aryl or heteroaryl substituents, which are usually attached at $R^1$, $R^3$, $R^6$, and/or $R^8$, preferably at $R^3$ and $R^6$.

In addition to the above substituents, each heteroaromatic ring of the ligand is optionally substituted by an additional fused aromatic ring. Any two adjacent heteroaromatic ring substituents taken in combination are optionally an additional fused aromatic ring; for example, $R^1$ and $R^2$ taken in combination, or $R^5$ and $R^6$ taken in combination. There are no more than two additional fused aromatic rings on the ligand, one on each heteroaromatic ring. Ligands that possess two additional fused aromatic rings may be symmetrically or unsymmetrically substituted. The fused aromatic ring substituents are independently and optionally substituted by halogen; sulfonic acid or salt of sulfonic acid; cyano; alkyl, perfluoroalkyl or alkoxy (each having 1–6 carbon atoms); amino; alkylamino (having 1–6 carbon atoms); dialkylamino (having 2–12 carbon atoms); carboxy; or carboxyalkyl, carboxyalkoxy, carboxyalkylamino, or carboxyalkylthio (each having 2–7 carbon atoms). Selected (but not exclusive) examples of some metal ion-binding moieties having additional fused rings are shown below.

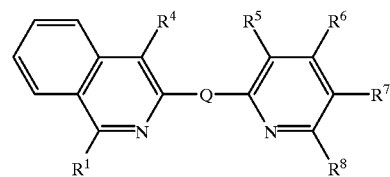

-continued

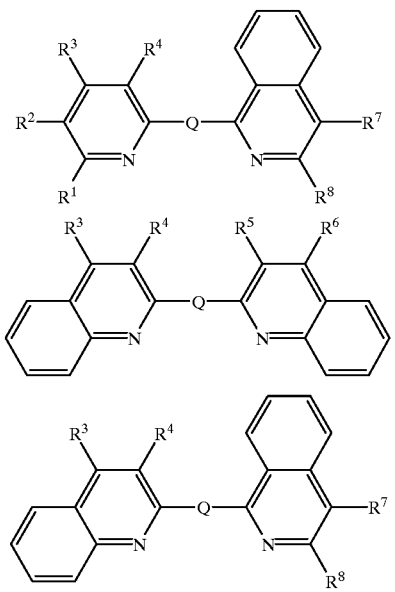

The aryl, heteroaryl, and additional fused ring substituents on the ligand optionally serve as attachment points for sulfonic acids or salts of sulfonic acids.

In one embodiment of the invention, Q is a single covalent bond, such that the resulting ligand is a bipyridyl-based chelator. Ligands that are bipyridyls have the general structure:

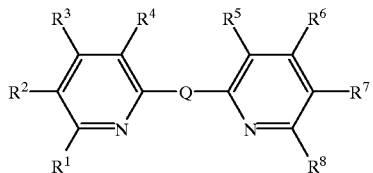

where $R^1$–$R^8$ are as defined previously.

In another embodiment of the invention, Q is a formal single bond, and $R^4$ and $R^5$ when taken in combination are —$CR^9$=$CR^{10}$–, such that the ligand is an aromatic phenanthroline-based chelator having the general formula:

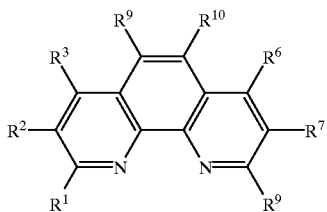

where $R^1$–$R^3$ and $R^6$–$R^8$ are as defined previously, and phenanthroline substituents $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbon atoms; a carboxy; or carboxyalkyl, carboxyalkoxy, carboxyalkylamino or carboxyalkylthio having 2–7 carbon atoms; an aryl or heteroaryl; halogen; or CN. Typically, one of $R^9$ and $R^{10}$ serves as the attachment point for a sulfonic acid or salt of sulfonic acid, and all other ring substituents are hydrogen, phenyl or phenyl substituted one or more times by a sulfonic acid or salt of sulfonic acid. Preferably, $R^3$ or $R^6$ or both are substituted by phenyl that is itself optionally substituted by a single sulfonic acid or salt of sulfonic acid.

When the ligand is a phenanthroline-based chelator, adjacent heteroaromatic ring substituents are optionally combined to form additional fused aromatic rings, excepting that $R^4$ and $R^5$ are no longer available to form additional fused rings with $R^3$ and $R^6$, respectively. Additional fused aromatic rings are therefore only available using combinations of $R^1$, $R^2$, $R^3$, $R^6$, $R^7$ and $R^8$. Typically the phenanthroline-based ligand does not contain additional fused rings.

In another embodiment of the invention, Q is —$(CR^{11}{}_2)_a$—$X_b$—$(CR^{12}{}_2)_c$—, such that the ligand is a bis-pyridyl-based chelator. In this embodiment, a, b and c are each 0 or 1. Selected examples of bis-pyridyl-based ligands are shown below.

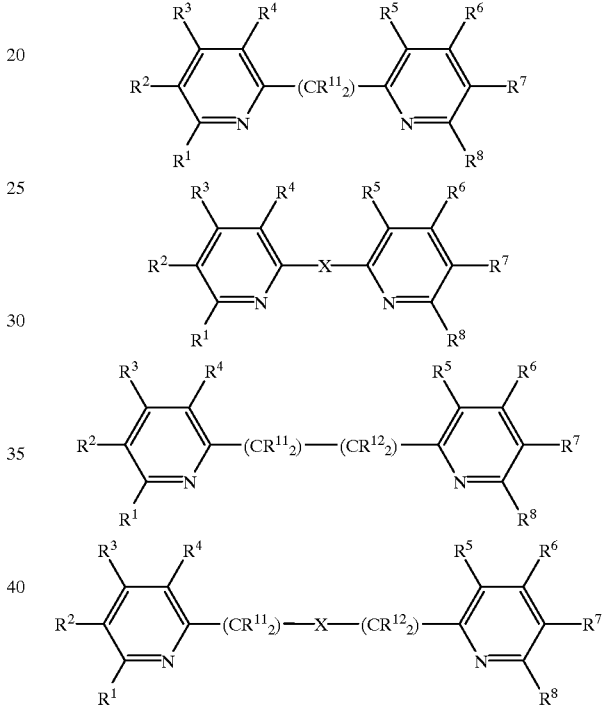

Each $R^{11}$ and $R^{12}$ is optionally and independently H or alkyl having 1–6 carbon atoms. Typically, each $R^{11}$ and $R^{12}$ is hydrogen.

The element X is optionally O or S, yielding an ether or thioether bridge, respectively. Alternatively, X is $NR^{13}$, where $R^{13}$ is H, $C_1$–$C_6$ alkyl. Alternatively, $R^{13}$ is phenyl that is optionally further substituted one or more times in any combination by alkyl, perfluoroalkyl, or alkoxy having 1–6 carbon atoms; sulfonic acid, salt of sulfonic acid; amino, alkylamino or dialkylamino, where each alkyl group has 1–6 carbon atoms; carboxy; carboxyalkyl, carboxyalkoxy, carboxyalkylamino or carboxyalkylthio having 2–7 carbon atoms; halogen, or CN. In yet another embodiment, X is —$CR^{14}R^{15}$—, yielding a trimethylene bridge, where $R^{14}$ and $R^{15}$ are independently H or alkyl having 1–6 carbon atoms. Additionally, either of $R^{14}$ and $R^{15}$ optionally serves as an attachment point for a sulfonic acid or salt of sulfonic acid. Typically, Q is —$CR^{11}{}_2$—$NR^{13}$—$CR^{12}{}_2$—, and $R^{13}$ is phenyl or substituted phenyl. Where $R^{13}$ is phenyl or substituted phenyl, it is optionally substituted by sulfonic acid or salt of sulfonic acid, as shown below:

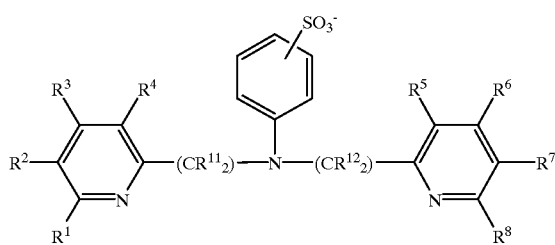

In an alternate embodiment of the invention, Q is a 2,6-disubstituted pyridyl, to yield a ligand having a terpyridyl-based complexing group, according to the following structure:

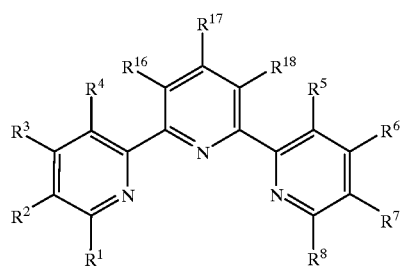

where $R^1$–$R^4$ and $R^5$–$R^8$ are as defined previously. In this embodiment, the substituents $R^{16}$, $R^{17}$, and $R^{18}$ are independently H; alkyl, perfluoroalkyl, or alkoxy having 1–6 carbon atoms; sulfonic acid, salt of sulfonic acid; amino, alkylamino or dialkylamino, where each alkyl group has 1–6 carbon atoms; carboxy; or carboxyalkyl, carboxyalkoxy, carboxyalkylamino, or carboxyalkylthio having 2–7 carbon atoms; halogen, or CN. Alternatively, one or more of $R^{16}$, $R^{17}$, and $R^{18}$ serves as the attachment point for sulfonic acid or salt of sulfonic acid. Typically $R^{16}$, $R^{17}$, and $R^{18}$ are hydrogen or sulfonic acid. Preferably $R^{16}$ and $R^{18}$ are hydrogen and $R^{17}$ is sulfonic acid.

For all embodiments, one of the ligands on the resulting metal complex must be substituted by at least one anionic moiety, and the net overall charge of the metal-ligand complex must be neutral or negative. Some particularly preferred embodiments of the invention are depicted graphically below (Compounds 1–8):

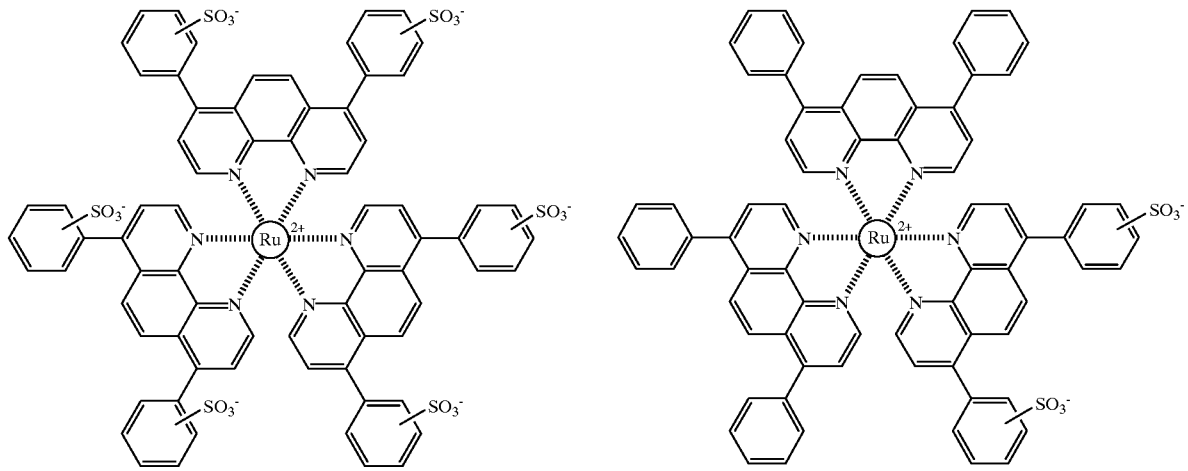

Compound 1

Compound 2

-continued
Compound 3
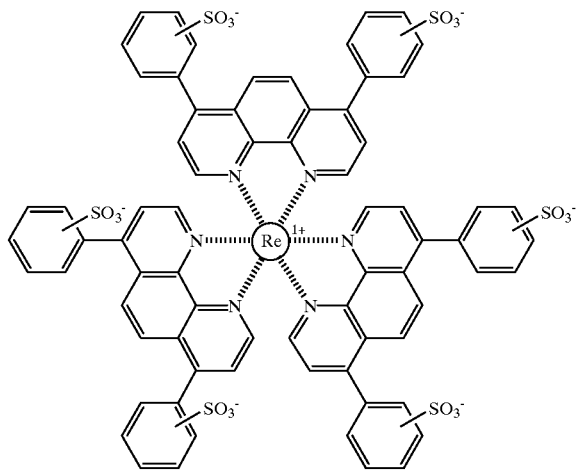
Compound 4
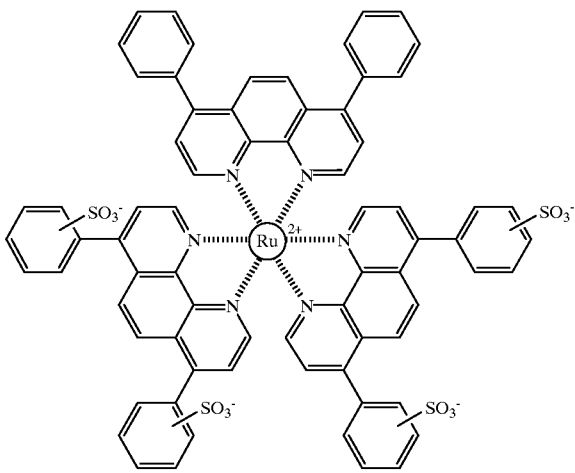
Compound 5
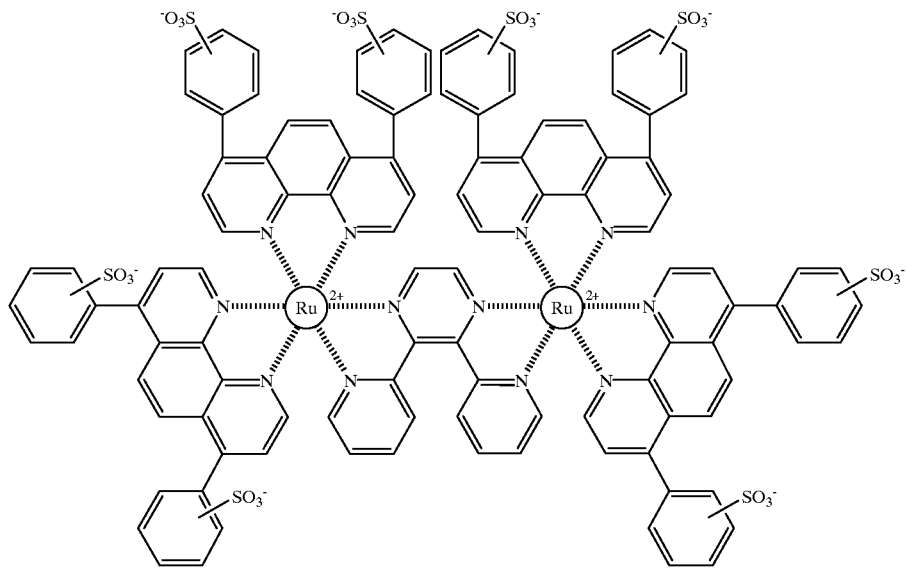
Compound 6
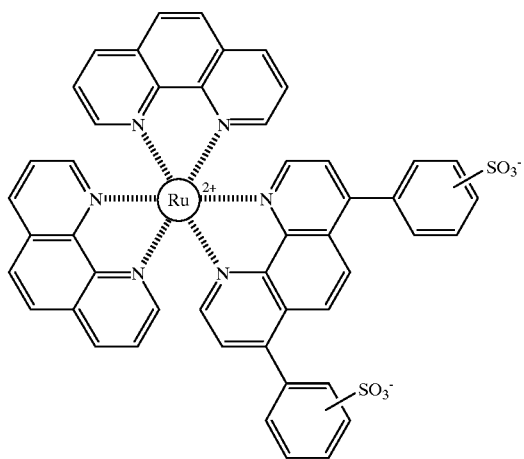
Compound 7
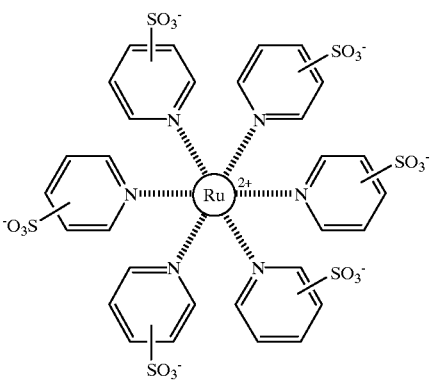

-continued

Compound 8

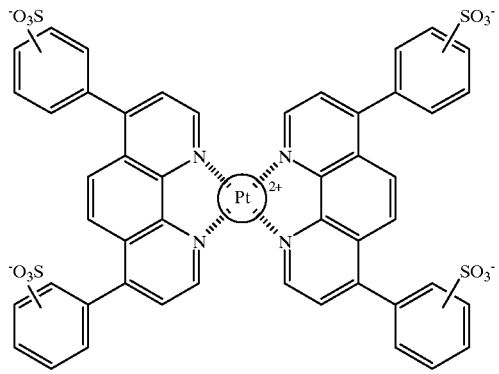

Synthesis of the Metal Complex

The preparation of transition metal complexes of nitrogen donor ligands is well known in the art. Amines, aromatic nitrogen heterocycles, and other derivatives of ammonia are classical ligands in coordination chemistry, and typically bind to transition metals via electron pair donation from the nitrogen atom. Ligands that possess more than one nitrogen atom that can bind to a metal atom are known as polydentate ligands. Classical examples of polydentate nitrogen-based ligands include, among others, ethylenediamines, tetramethylethylenediamines, pyridines, bipyridyls, terpyridyls, quinolines, and phenanthrolines. These nitrogen donor ligands are good ligands for transition metals over a range of oxidation states (see for example McWhinnie et al., ADV. INORG. CHEM. RADIOCHEM. 12, 135 (1969)).

The preparation of transition metal complexes of such nitrogen donor ligands is well described in the chemical literature. The typical synthesis consists of mixing, and if necessary, heating a solution of the appropriate metal chloride in the presence of the desired nitrogen donor ligand. Mixed ligand complexes are typically prepared by heating the metal chloride in the presence of a mixture of the desired ligands in the desired ratios. The resulting products typically occur in a statistical distribution, and can be isolated by methods known in the art. Alternatively, the chloride ions are displaced in a stepwise fashion by the selected ligands, resulting in the controlled synthesis of the desired isomer. Similarly, the use of a ligand that possesses more than one metal binding site results in polymetallic complexes (for example, Compound 5).

Representative examples of the preparation of metal complexes with nitrogen donor ligands are found in Szmacinski et al. (BIOCHIMICA ET BIOPHYSICA ACTA 1383, 151 (1998)), Castellano et al. (PHOTOCHEMISTRY AND PHOTOBIOLOGY 67(2), 179 (1998)), Schwarz et al. (J. PHOTOCHEM. PHOTOBIOL 112, 47 (1998)), Bard et al. (U.S. Pat. No. 5,731,147 (1998)), and Moucheron et al. (J. AM. CHEM. SOC. 118, 12834 (1996)).

Many ligands suitable for use in the instant invention are commercially available. Where a desired ligand is not readily available, it is often readily prepared by synthetic modification of the ligand prior to complexation with the metal, typically by sulfonation. Sulfonation of heteroaromatic ligands occurs by methods well known in the art, typically using sulfuric acid, fuming sulfuric acid, or chlorosulfonic acid. In the case of bipyridyl ligands, direct sulfonation is typically not effective. For example, sulfonated bipyridyls are typically prepared by thiolation of bipyridyl followed by oxidation to the sulfonic acid (for example, J. CHEM. SOC. DALTON TRANS. 2247 (1985)).

Method of Use

The present invention utilizes the metal complexes described above to stain poly(amino acids), followed by detection of the stained poly(amino acids) and optionally their quantification or other analysis. By poly(amino acid) is meant any assemblage of multiple amino acids, including homopolymers or heteropolymers of amino acids, that incorporate peptide linkages. Poly(amino acids), as used herein, include peptides and proteins. The poly(amino acids) are stained by combining a sample mixture that is thought to contain poly(amino acids), with a staining mixture that comprises one or more of the metal complexes described above that give a detectable colorimetric or luminescent optical response upon illumination, or that have a detectable intrinsic radioactivity. Additional steps are optionally and independently used in any combination, before, after or concurrently with staining, to provide for separation or purification of the poly(amino acids), for enhancing the detection of the poly(amino acids), for quantification of the poly(amino acids), for identification of a specific poly(amino acid) or group of poly(amino acids) such as by use of an antibody or lectin. The method of the instant invention is both generally and specifically useful in performing many aspects of proteomics, that is, the determination of an accurate profile of protein abundance, structure and activity in a given cell or tissue sample.

Without wishing to be bound by theory, it is presumed that the anionic moieties of the metal complexes of the invention associate electrostatically with aliphatic amines present on poly(amino acids), which are typically protonated and positively charged at or below physiological pH. Therefore the formulations and methods of the invention are useful for the detection and quantification of other substances that possess primary amines, such as lipopolysaccharides. Metal complexes that are overall positive in ionic charge are undesirable or unsuitable for poly(amino acid) staining, and are not included in the scope of materials useful for the present invention.

Typically, the present invention is utilized to detect poly(amino acids) by combining a sample mixture that is thought to contain a poly(amino acid) with a staining mixture that contains one or more of the metal complexes of the invention to form a combined mixture. The combined mixture is then incubating for a time sufficient for the metal complex in the staining mixture to associate with any poly(amino acid) present in the sample mixture. The resulting stained poly(amino acids) complex are then illuminated at a wavelength where the selected metal complex is excited, and the resulting optical response is detected.

Sample Mixture

The sample mixture contains or is suspected to contain poly(amino acids). The sample mixture optionally further comprises an aqueous solution, typically prepared with water (e.g. for pure proteins) or aqueous buffer, or is combined with an aqueous solution in the course of labeling. By aqueous solution is meant a solution that is predominantly water and retains the solution characteristics of water. Where the aqueous solution contains solvents in addition to water, water is typically the predominant solvent.

Typically the sample mixture is present on or in a solid or semi-solid matrix. In one embodiment, the solid or semi-solid matrix comprises a membrane, such as a filter membrane. In another embodiment, the solid or semi-solid matrix comprises an electrophoresis medium, such as a polyacrylamide gel, agarose gel, linear polyacrylamide solution, polyvinyl alcohol gel, or capillary electrophoresis buffer. In one embodiment of the invention, the solid or semi-solid matrix comprises a membrane, such as a nitrocellulose or poly(vinylidene difluoride) membrane, wherein the poly (amino acids) are immobilized on the membrane by blotting, spotting, or other method of application.

The poly(amino acids) that are suitable for staining using this method include both synthetic and naturally occurring poly(amino acids), comprising both natural and unnatural amino acids. The poly(amino acids) of the invention include peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly(amino acids). In one aspect of the invention, the poly(amino acids) contain at least one basic amino acid such as lysine, arginine or histidine. In another aspect of the invention the poly(amino acids) are enzymes, antibodies, transcription factors, secreted proteins, structural proteins, nuclear protein, or binding factors, or combinations thereof. In yet another aspect of the invention, the poly (amino acids) comprise the proteome of a cell.

The poly(amino acids) in the sample mixture are optionally covalently or non-covalently bound to a solid or semi-solid surface, such as a glass slide, multi-well plate (such as a 96 well plate), plastic pin, polymeric membrane or bead, or semiconductor material, or they are unbound. The staining of a poly(amino acid) that is bound to an analyte on a solid surface indicates the presence of the analyte as well as that of the poly(amino acid).

The poly(amino acids) are obtained from a variety of sources; such sources including biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids. In one embodiment, the poly(amino acids) comprise the proteome of an animal cell, typically a mammalian cell.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample mixture by mobility (e.g. electrophoretic gel or capillary) or by size (e.g. centrifugation, pelleting or density gradient), or by binding affinity (e.g. to a filter membrane or affinity resin) in the course of the method. In another aspect of the invention, the sample mixture thought to contain the poly(amino acids) has undergone separation. In yet another aspect of the invention, the poly(amino acids) are not separated. In one embodiment, the sample mixture is essentially cell-free. In another embodiment, the sample mixture comprises viable cells, non-viable cells, cellular organelles such as nuclei or mitochondria, or a mixture thereof In another embodiment of the invention, the sample mixture comprises tissues, tissue slices, tissue smears, entire organs, or organisms. In yet another embodiment of the invention, the components of the sample mixture are physically separated before or while it is combined with the staining mixture, including but not limited to separation by flow cytometric, electrophoretic, or microfluidic methods. Where the components of the sample mixture include cells, the cells are optionally separated based on their detectable optical response, which is then correlated to cell viability (Example 23).

The poly(amino acids) are optionally unmodified, or have been treated with a reagent or molecular composition so as to enhance or decrease the mobility of the poly(amino acid) in an electrophoretic gel. Such reagents may modify poly (amino acids) by complexing with the peptide (typically to decrease migration), by cleaving selected peptide bonds (typically to increase migration of the resulting fragments), by changing the relative charge on the protein (such as by acylation, phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly(amino acids) having the same original composition, so that the distribution of the poly(amino acid) indicates the presence of another analyte.

Typically the poly(amino acids) in the sample mixture have a molecular weight greater than about 500 daltons. More typically the poly(amino acids) are more than 800 daltons. The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. Typically, such a mixture contains equal mass quantities of myosin, β-galactosidase, phosphorylase B, bovine serum albumin, ovalbumin, carbonic anhydrase, trypsin inhibitor, lysozyme and aprotinin. The metal complexes of the present invention also stain low molecular weight peptides, polypeptides and proteins, such as insulin, aprotinin, or neuropeptides. The metal complexes of the invention can stain very small peptides, even peptides as small as a 15-mer or 7-mer (Example 20). Staining of small peptides is typically enhanced where the peptide contains one or more basic amino acid residues.

In on embodiment of the invention, separated poly(amino acids) in electrophoretic gels are post-stained using the staining mixture, or are transferred to a filter membrane or blot or other solid or semi-solid matrix before being combined with the staining mixture. The present method is effective for both denaturing and non-denaturing gels. Denaturing gels optionally include a detergent such as SDS or other alkyl sulfonate (e.g. 0.05%–0.1% SDS). Typically, polyacrylamide or agarose gels are used for electrophoresis. Commonly used polyacrylamide gels include but are not limited to Tris-glycine, Tris-tricine, mini- or full-sized gels, generally possessing a stacking gel. Agarose gels include modified agaroses. Alternatively, the gel is an iso-electric focusing gel or strip. In addition to polyacrylamide and agarose gels, suitable electrophoresis gels are optionally prepared using other polymers, such as HYDROLINK. Alternatively, the electrophoretic gel is a gradient gel. Useful electrophoretic gels for the present invention are either prepared according to standard procedures or are purchased commercially.

In another embodiment of the invention, the present method is used to detect poly(amino acids) present in a two-dimensional electrophoretic gel. In another embodiment of the invention, the electrophoretic gel is used for gel-mobility-shift analysis, where a polyacrylamide or agarose gel is cast and run in a buffer optimized to preserve the specific protein/nucleic acid interaction of interest. In both embodiments, the staining mixture is optionally combined with the sample mixture at any stage in the electrophoresis procedure, but the dyes are preferably used following electrophoretic separation as a post-stain.

Many conventional electrophoresis gel staining techniques, such as ammoniacal silver staining, are unsuitable for pH-neutral gels, such as commercially available pre-cast gels that incorporate Tris-tricine and Tris-bicine, due to excessively high background staining. In contrast, the present method stains pH-neutral gels with high sensitivity. Even large gels that incorporate a plastic backing, or that are prepared using a gel strengthening agent (such as DURACRYL or ACRYLAIDE) are stained effectively using the present method.

Where the sample mixture is on or in an electrophoretic gel or a blot membrane, the poly(amino acids) of the sample mixture are typically present at a concentration of 1 ng/band –4 µg/band.

In yet another embodiment of the invention, the present method is used to detect poly(amino acids) that are themselves associated with a target of interest. For example, a target molecule is labeled with biotin, which is then labeled with streptavidin using standard immunological methods. The streptavidin is then stained using a metal complex of the invention. Luminescent detection of the streptavidin results in detection and/or localization of the target of interest. Similarly, a target can be labeled with a polypeptide, which is then directly detected using a metal complex of the invention. The use of time-resolved detection methods allows for sensitive detection of even small amounts of target.

Staining Mixture

In order to effect poly(amino acid) staining, the sample mixture is combined with a staining mixture. A staining mixture is typically prepared by dissolving a selected metal complex in a solvent, such as water, DMSO, DMF or methanol, usually to a metal complex concentration of 1–10 µM. The complexes of the invention typically possess good aqueous solubility, particularly where there are 4–6 anionic moieties present on the complex. These complexes usually do not require dissolution into organic solvents prior to preparing the aqueous solution. The concentrated stock solution is generally diluted with an aqueous solution according to the assay being performed. Staining solutions can be stored and reused for months without signal loss. For staining poly(amino acids) on gels or membranes, the metal complex is diluted into a solution that comprises water, and optionally further comprises additional formulation components, such as acids, buffering agents, inorganic salts, polar organic solvents, antioxidants, and ion chelators.

Although the instant method of staining is most useful when used in conjunction with detection of luminescence, some metal complexes used for the invention have calorimetric absorbance and can be detected, albeit with lower sensitivity, by their visible color absorbance. For luminescence detection, the staining mixture comprises the metal complex at a typical concentration of greater than 0.10 µM and less than 10 µM; preferably greater than about 0.50 µM and less than or equal to about 5 µM; more preferably 1–3 µM. Where the staining method of the invention is being utilized to determine cell viability, the metal complex is typically present in a concentration of about 1–5 µM, preferably about 3 µM. In one embodiment, the metal complex is present at a concentration of about 1.5 µM. In another embodiment, the metal complex is present at a concentration of about 5 µM.

A particular metal complex is generally selected for a particular assay using one or more of the following criteria: sensitivity to poly(amino acids) in general or to a specific class thereof, dynamic range, photostability, staining time, and insensitivity to the presence of nucleic acids. Preferably, the metal complexes of the present invention are capable of detecting 1–2 ng or less of poly(amino acid) per band in electrophoretic gels.

The metal complexes of the invention readily stain proteins at a wide variety of pH values. Typically the staining mixture has a pH of about 1 to about 10, more typically the staining mixture has a pH of about 4 to about 9. The pH of the staining mixture can be controlled by the selection of appropriate acidic components or buffering agents.

Where the presence of an acidic component in the staining mixture is desirable, any acidic component that is compatible with poly(amino acids) is a suitable acidic component. Typical suitable acidic components include without limitation acetic acid, trichloroacetic acid, trifluoroacetic acid, perchloric acid, phosphoric acid, or sulfuric acid. The acidic component is typically present at a concentration of 1%–20%. Where the acidic component is acetic acid, it is typically present at a concentration of 5%–10%. Where the acidic component is trichloroacetic acid, it is typically present at a concentration of 7%–30%, preferably 10%–20%, more preferably 12%–13%. Where the acidic component is perchloric acid, it is typically present at a concentration of 2–5%. Where the acidic component is phosphoric acid, it is typically present at a concentration of 1%–5%.

The pH of the staining mixture is optionally modified by the inclusion of a buffering agent in addition to or in place of an acidic component. In particular, the presence of a buffering agent has been shown to improve staining of electrophoretic gels, provided that an alcohol and an inorganic salt are included in the formulations as well. Any buffering agent that is compatible with the poly(amino acids) in the sample is suitable for inclusion in the staining mixture.

In one embodiment, the buffering agent is one of the so-called "Good" buffers. "Good" buffers include BES (N,N-bis[2-hydroxyethyl]-2-aminoethanesulfonic acid; 2-[bis(2-hydroxyethyl)amino]ethanesulfonic acid); BICINE (N,N-bis[2-hydroxyethyl]glycine), CAPS (3-[cyclohexylamino]-1-propanesulfonic acid), EPPS (N-[2-hydroxyethyl]piperazine-N'-[3-propanesulfonic acid]), HEPES ((N-[2-hydroxyethyl]piperazine-N'-[2-ethanesulfonic acid]), MES (2-[N-morpholino] ethanesulfonic acid), MOPS (3-[N-morpholino] propanesulfonic acid), PIPES (piperazine-N,N'-bis[2-ethanesulfonic acid]; 1,4-piperazinediethanesulfonic acid), TAPS (N-tris[hydroxymethyl]methyl-3-aminopropanesulfonic acid; ([2-hydroxy-1,1-bis (hydroxymethyl)ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino) ethanesulfonic acid), or TRICINE (N-tris[hydroxymethyl] methylglycine; N-[2-hydroxy-1,1-bis(hydroxymethyl)ethyl] glycine).

Other useful buffering agents include salts of formate, citrate, acetate, 2-(N-morphilino) ethanesulfonic acid, imidazole, N-2-hydroxyethyl-piperazine-N'-2-ethanesulfonic acid, Tris (hydroxymethyl)aminomethane acetate, or Tris (hydroxymethyl)aminomethane hydrochloride. In a preferred embodiment, the buffering agent is sodium acetate. The buffering agent is typically present in the staining mixture at a concentration of 20 mM to 500 mM, in another aspect at a concentration of 50 mM to 200 mM, and in another aspect at a concentration of about 100 mM.

Any inorganic salt that is adequately soluble in the formulation itself may be used in the staining formulations. Advantageous inorganic salts produce staining formulations that exhibit low background signals in stained gels. Typically, the inorganic salt dissolves to yield at least one ion having multiple charges, such as a magnesium salt. Particularly useful and inexpensive salts include ammonium sulfate, magnesium chloride, zinc chloride, magnesium sulfate and magnesium glucuronate present in the staining mixture at a concentration of 1–50%. In one embodiment, the inorganic salt is ammonium sulfate or magnesium chloride. In another embodiment, the inorganic salt is magnesium chloride. Magnesium chloride is typically present in the staining mixture at a concentration of about 4–45%, or about 5%–20%, or about about 6%–10%. In one embodiment, the magnesium chloride is present at a concentration of about 8%.

Inclusion of a polar organic solvent, typically an alcohol, in the staining mixture is recommended. While the use of highly polar solvents such as formamide is permitted, typically, the polar organic solvent is an alcohol having 1–6 carbon atoms, or a diol or triol having 2–6 carbon atoms. The polar organic solvent, when present, is typically included in the staining mixture at a concentration of 5–50%. The presence of a polar organic solvent is particularly advantageous when staining sodium dodecyl sulfate-coated proteins, as is typically the case when staining poly(amino acids) that have been electroblotted from SDS-polyacrylamide gels. Without wishing to be bound by theory, it appears that the presence of an alcohol improves luminescent staining of poly(amino acids) due to the removal of SDS from the protein. However, nitrocellulose membranes may be damaged by high concentrations of alcohol (for example, greater than 20%), and so care should be taken to select solvent concentrations that do not damage the membranes present in the sample mixture.

Certain acid- and alcohol-containing formulations of Coomassie Blue dye cause irreversible acid-catalyzed esterification of glutamic acid side chain carboxyl groups of sample proteins, while formaldehyde, present in many silver staining formulations, leads to alkylation of $\alpha$- and $\epsilon$-amino groups. Such modifications hinder the subsequent identification of proteins by mass spectrometry by complicating the interpretation of spectra or by reducing peptide recovery. With respect to the present invention, the use of staining mixtures that include trichloroacetic acid in combination with either methanol or ethanol has resulted in significant acid-catalyzed esterification of glutamic acid as determined by matrix-assisted laser desorption mass spectrometry.

This undesirable modification of proteins by the staining mixture is prevented by selection of a less reactive alcohol for inclusion in the staining mixture. The use of low molecular weight diols and triols as the polar organic solvent results in several advantages for the instant method. First, the esterification of sample proteins is eliminated. Additionally, low molecular weight diols and triols are substantially less flammable than alcohols such as methanol and ethanol, resulting in staining mixtures that are safer to use in a laboratory setting. In one embodiment, the polar organic solvent is a diol or triol having 2–6 carbon atoms. In one aspect of the invention, the polar organic solvent is glycerol, glycolic acid, or a diol having 2–6 carbon atoms. More preferably, the polar organic solvent is a diol that is 1,2-ethanediol or 1,2-propanediol. The polar organic solvent is typically present at a concentration of 5–50%. In one embodiment particularly useful for staining isoelectric focusing gels, the polar organic solvent is a diol that is present at a concentration of 5–30%, or at a concentration of 5–15%. In another embodiment particularly preferred for staining electrophoresis gels, the polar organic solvent is a diol that is present at a concentration of 30–40%, or at a concentration of 33–36%.

Staining of poly(amino acids) is optionally enhanced by the addition of an antioxidant or a metal ion chelator. Selected embodiments of antioxidants include glucuronic acid, ascorbic acid and citric acid. Selected embodiments of metal ion chelators include ethylenediamine diacetic acid, ethylenediamine tetraacetic acid (EDTA), ethylene glycol-bis-($\beta$-aminoethyl ether) tetraacetic acid (EGTA), citric acid, 1,2-bis-(2-aminophenoxyethane)-N,N,N',N'-tetraacetic acid (BAPTA), 2-carboxymethoxy-aniline-N,N-diacetic acid (APTRA), and various crown ethers. Citric acid may act as both an antioxidant and a chelating group, and is a particularly useful additive to the staining mixture.

Broadly speaking, two formulations of the staining mixture of the invention have been found to have highly effective staining properties. The first is similar to the staining formulation utilized for standard Coomassie Blue staining, and comprises 0 to 10% acid, such as acetic acid or formic acid, and 0 to 40% alcohol, such as methanol, ethanol, or diol having 2–6 carbon atoms. This formulation is especially suitable for staining poly(amino acids) present on membranes, such as dot-blots, slot-blots, or electroblots, as well as staining of cells on tissue prints, with little background staining. The second preferred class of formulations is similar to those employed for colloidal Coomassie Blue staining of gels.

When the metal complexes of the invention are prepared in formulations similar to those utilized for colloidal Coomassie Blue staining, the staining mixture stains poly(amino acids) in polyacrylamide gels with greatly reduced background staining. A low background level of luminescence is particularly important for quantitative measurements of poly (amino acid) bands, as any destaining procedure would invariably remove some staining from the poly(amino acid) band as well Selected staining formulations and their utility for staining electrophoretic gels are provided in Table 1.

TABLE 1

| Staining Formulation | Composition (in water) | Results of Electrophoretic Gel Staining |
|---|---|---|
| 1 | 17% magnesium chloride<br>2% phosphoric acid<br>34% methanol<br>1.5 µM Compound 2 | Low background luminescence<br>good protein staining |
| 2 | 1.5 µM Compound 2 | High background luminescence<br>poor protein staining |
| 3 | 17% ammonium sulfate<br>34% methanol<br>1.5 µM Compound 2 | Low background luminescence<br>good protein staining |
| 4 | 12.5% trichloroacetic acid<br>25% ethanol<br>1.5 µM Compound 2 | Low background luminescence,<br>Good protein staining |
| 5 | 17% ammonium sulfate<br>2% phosphoric acid<br>1.5 µM Compound 2 | Speckled luminescent background<br>poor protein staining |
| 6 | 2% phosphoric acid<br>34% methanol<br>1.5 µM Compound 2 | High background luminescence<br>good protein staining |
| 7 | 34% methanol<br>1.5 µM Compound 2 | High background luminescence<br>good protein staining |
| 8 | 17% acetic acid<br>10% methanol<br>1.5 µM Compound 2 | High background luminescence<br>good protein staining |
| 9 | 12.5% trichloroacetic acid<br>25% 1,2-propanediol<br>1.5 µM Compound 2 | Low background luminescence<br>good protein staining |

As shown above, staining formulations 1 and 3 provide sensitive luminescent detection of proteins in SDS-polyacrylamide gels accompanied by low background staining. Unlike colloidal Coomassie Blue stain, there is no requirement for an acidic solvent environment. Formulations 6–8 are similar to standard non-colloidal formulations of Coomassie Blue, and produce staining of the gel matrix, requiring a gel destaining step for In the other formulation (12.5% trichloroacetic acid, 25% methanol), low background protein staining is also achieved. Decreasing the concentration of the alcohol to 10% or 2.5% results in an accompanying increase in background staining of the gel matrix. Replacement of methanol with ethanol or 1,2-propanediol does not adversely affect staining (formulations 4 and 9). Omission of trichloroacetic acid, however, yields results similar to formulation 6 (high background staining). Therefore, preferred staining mixtures include both an acidic component and an alcohol or diol.

In one embodiment, the staining mixture comprises about 1.5 µM metal complex of the invention, about 34% 1,2-propanediol, about 8% magnesium chloride, and about 100 mM sodium acetate at pH 4. In another preferred embodiment having particular utility for staining poly(amino acids) present in isoelectric focusing gels, the staining mixture comprises about 1.5 µM metal complex of the invention, about 12.5% trichloroacetic acid and about 25% 1,2-propanediol. In another preferred embodiment having particular utility for staining poly(amino acid) dot blots and electroblots, the staining mixture comprises about 5 µM of a metal complex of the invention, about 100 mM sodium acetate at pH 4, and about 75 µM citric acid. In another preferred embodiment having particular utility for detecting or counterstaining cultured cells or tissue sections, the staining mixture comprises 1–5 µM of a metal complex of the invention, and about 7% acetic acid.

Combined Mixture

The staining mixture is combined with the sample mixture in such a way as to facilitate contact between the metal complex and any poly(amino acids) present in the combined mixture. Without wishing to be bound by theory, it is believed that the negatively charged anionic moieties present on the metal complexes of the invention interact non-covalently by electrostatic attraction with primary amines present on the poly(amino acids) in the sample mixture, which are generally protonated at pH levels less than 10.

Destaining of stained gels is typically not necessary for luminescent detection of proteins using the metal complexes of the invention, although for certain staining formulations containing methanol/acetic acid, destaining typically improves poly(amino acid) detection in gels. For example, while staining of proteins in polyacrylamide gels is typically accompanied by some background staining of the gel matrix, such background staining can be reduced by incubation of the stained gel in a comparable formulation comprising an acid and an alcohol that does not contain the staining metal complex. This incubation typically removes dye from the gel background, with little loss of protein staining. Stained gels may also be washed briefly after staining to prevent transfer of the staining metal complex to other surfaces. The duration of staining is such that stained gels can be photographed months after staining without significant loss of signal.

Electrophoretic gels stained according to the method of the invention can subsequently be dried onto filter paper or between plastic sheets (e.g. cellophane), using standard procedures.

Where the staining method of the invention is being utilized to determine cell viability, the sample mixture is typically incubated with the staining mixture of the invention for about 5–10 minutes, preferably 5–6 minutes. Where the staining method of the invention is being utilized to stain tissue prints or cells on microscope slides, the sample mixture is typically incubated with the staining mixture of the invention for about 5–60 minutes, preferably for 10–30 minutes, more preferably for about 15 minutes.

Additional Reagents

The method of the present invention optionally further comprises one or more additional reagents that are simultaneously or sequentially combined with the sample mixture, the staining mixture, or the combined mixture. An additional reagent is optionally a detection reagent that colocalizes with poly(amino acids) in general or with specific poly(amino acids) to enhance the detection thereof by the method of the present invention. Alternatively, the additional reagent is useful for identification of other components in the sample mixture, such as a nucleic acid stain, or a stain for lipids or carbohydrates. Or, the additional reagent is a detection reagent designed to interact with a specific portion of the sample mixture, so as to probe for a specific component of the sample mixture, where spatial coincidence of the metal complex and the detection reagent indicates that the additional reagent is also associated with the poly(amino acids).

The additional reagent also incorporates a means for producing a detectable response. A detectable response means a change in, or occurrence of, a parameter in a test system that is capable of being perceived, either by direct observation or instrumentally. Such detectable responses include the change in, or appearance of, color, fluorescence, reflectance, pH, chemiluminescence, infrared spectra, magnetic properties, radioactivity, light scattering, x-ray scattering, or the precipitation of an electron-rich substrate. Appropriate labels to provide a detectable response include, but are not limited to, a visible or fluorescent dye, a chemiluminescent reagent, an enzyme substrate that produces a visible or fluorescent precipitate upon enzyme action (for example, the action of horseradish peroxidase upon diaminobenzidine, or enzyme action on a labeled tyramide), visible or fluorescent labeled microparticles, a metal such as colloidal gold, or a silver-containing reagent, or a signal that is released by the action of light upon the reagent (e.g. a caged fluorophore that is activated by photolysis, or the action of light upon diaminobenzidine). The detectable label of the additional reagent is detected simultaneously or sequentially with the optical signal of the complexes of the present invention.

In one embodiment of the invention, one or more additional metal complexes, including preferred embodiments described above, are the additional reagent(s). The individual metal complexes may be selected to exhibit overlapping spectral characteristics, such that energy transfer occurs between the complexes associated with the poly(amino acids), resulting in labeled poly(amino acids) that exhibit an extended Stokes shift. Alternatively, the additional dye(s) colocalize with the metal complex such that the labeling of some or all poly(amino acids) exhibits quenching. Alternatively, the additional reagent is another protein stain (such as CBB or silver stain) such that labeling of the poly(amino acids) is enhanced by the colocalization of staining.

Other useful additional reagents are fluorescent nucleic acid stains. A variety of appropriate nucleic acid stains are known in the art, including but not limited to, thiazole orange, ethidium homodimer, ethidium bromide, propidium iodide, HOECHST 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et al., 1994; or U.S. Pat. No. 5,410,030 DIMERS OF UNSYMMETRICAL CYANINE DYES CONTAINING PYRIDINIUM MOIETIES to Yue et al., 1995. The use of an appropriate nucleic acid stain in conjunction with the dyes of the present invention can be selected to allow simultaneous or sequential observation of poly(amino acids) and nucleic acids such as DNA and RNA.

In one embodiment, the additional reagent comprises a member of a specific binding pair having a detectable label. Representative specific binding pairs are shown in Table 2.

TABLE 2

Representative specific binding pairs

| | |
|---|---|
| enzyme | enzyme substrate |
| antigen | antibody |
| biotin | avidin (or streptavidin) |

TABLE 2-continued

Representative specific binding pairs

| | |
|---|---|
| IgG* | protein A or protein G |
| carbohydrate | lectin |

*IgG is an immunoglobulin

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

In another embodiment of the invention, an electrophoresis gel stained according to the method of the invention may be imaged, and subsequently incubated with a detection reagent that is a primary antibody. The resulting immuno-labeled gel is then restained according to the method of the invention. The metal complex of the invention will associate with and stain the primary antibody just as it stains other poly(amino acids), and thereby increase the overall staining of the gel. In this embodiment, even an unlabeled antibody could be used for immunolabeling, as the presence of the label does not appreciably effect staining by the instant complexes. This methodology is particularly useful for high-throughput image analysis, permitting automated workstations to rapidly screen stained gels for spots that increase in intensity upon labeling and restaining. The staining of other poly(amino acid) labels, for example actin that is used to identify actin-binding proteins, is readily accomplished in the same manner.

As an example of an application of an additional detection reagent, a significant problem in two-dimensional gel electrophoresis is the alignment of a target protein detected using antibody-based or lectin-based methods with the entire constellation of species resolved by 2-D electrophoresis. Known protein stains, such as Amido Black and CBB staining, are difficult to destain, prevent subsequent immunostaining, and are generally difficult to use in this application. The staining method of the instant invention permits facile luminescent two-color detection in 2-D electrophoresis gels. As an example, 2-(5'-chloro-2-phosphoryloxyphenyl)-6-chloro-4(3H)-quinazolinone (U.S. Pat. No. 5,316,906 to Haugland et al. (1994)) produces a photostable, fluorescent yellow-green precipitate that is spectrally complementary to the ruthenium (II) complexes of the invention. The use of alkaline phosphatase-conjugated antibodies to detect target proteins in conjunction with Compound 1, for example, permits two color visualization of proteins in a single gel or electroblot. The appropriate selection of emission filters allows spectral separation of signal from the target protein and the total protein profile. It is possible to select fluorophores for the detection of specific classes of proteins, such as glycoproteins, lipoproteins or phosphoproteins that are spectrally well suited for use in combination with the metal complexes of the invention.

Illumination and Observation

Where the metal complex of the invention incorporates a radioactive metal ion (such as an α- or β-emitter), the presence and location of the metal complex in the combined mixture is optionally detected by radiography. Typically, intrinsic radioactivity is detected using film, phosphor storage plates, or microscanner array detectors.

The metal complex is most typically detected by its intrinsic luminescence. After addition of the metal complex to the sample mixture, the sample mixture is illuminated by a light source capable of exciting the stained sample mixture. Typically, the sample mixture is excited by a light source capable of producing light at or near a wavelength of peak absorption of the metal complex, such as an ultraviolet or visible wavelength emission lamp, an arc lamp, a fluorescent bulb, or even an incandescent bulb. Typically, ultraviolet excitation of the metal complex occurs at 250–370 nm, while visible excitation occurs at 450–540 nm. Preferably the sample mixture is excited with a wavelength within 20 nm of the maximum absorption of the metal complex. Although excitation by a source more appropriate to the maximum absorption band of the metal complex may result in higher sensitivity, the equipment commonly available for excitation of fluorescent samples can be used to excite the stains of the present invention. Selected equipment that is useful for illuminating the metal complex includes, but is not limited to, ultraviolet trans-illuminators, ultraviolet epi-illuminators, hand-held ultraviolet lamps, mercury arc lamps, xenon lamps, argon-ion lasers, diode lasers, and Nd-YAG lasers. These illumination sources are optionally integrated into laser scanners, fluorescence microplate readers, standard or mini fluorometers, microscopes, flow cytometers, gel readers, or chromatographic detectors.

As the metal complexes of the invention possess long-lifetime luminescence, observation of luminescence may occur at greater than ~100 nanoseconds after illumination, even up to greater than 10 microseconds after illumination (see Example 4). Utilizing this 'time-resolved' luminescence results in the exclusion of almost all of the sources of background fluorescence, which is typically short-lived. This property is particularly useful where samples are intrinsically fluorescent, have fluorescent impurities, or in combination with other detection reagents that give prompt fluorescence.

Some transition metal complexes, including complexes of ruthenium (II), exhibit luminescence quenching in the presence of oxygen. Without wishing to be bound by theory, the close association of the metal complexes of the invention with poly(amino acids) appears to shield the metal ions of the invention from oxygen quenching, resulting in brighter luminescence. Exclusion of oxygen from the combined mixture can result in an enhanced level of background luminescence, as metal complexes that are not associated with poly(amino acids) are dequenched. Conversely, the addition of primary amine-containing dendrimers to stained blots results in an enhancement of luminescence, presumably due to the dendrimers providing additional shielding of the metal ions from oxygen.

In another embodiment of the invention, the presence or amount of poly(amino acids) in the sample mixture is detected by measuring the polarization of the luminescence of the metal complexes of the invention. The technique of fluorescence polarization involves exciting a fluorescent- or luminescent-labeled sample mixture with polarized light, and measuring the polarization of the resulting fluorescence. Where the labeled molecule is large and rotates slowly (such as stained poly(amino acids)), the change in polarization between the excitation light and the resulting fluorescence is very small. Where the labeled molecule is small and rotates rapidly (such as the metal complex in the absence of poly(amino acids)), the change in polarization is large. Fluorescence polarization assays typically use samples that are homogenous solutions.

In one aspect of the invention, the metal complexes of the present invention possess an absorption maximum between 250–370 nm in the ultraviolet region, and/or between 440–550 nm in the visible region. In another aspect, the metal complexes of the present invention are selected such that the absorption maximum of the metal complex matches the wavelength of a laser illumination source. Typically such complexes have absorption maxima within 10 nm of 405 nm, 454 nm, 488 nm, 514 nm, 543 nm, 568 nm, or 590 nm. In another aspect of the invention, the complexes of the present invention excite efficiently in the ultraviolet wavelength range, more preferably at or near 300 nm, 365 nm, and/or 254 nm.

The detectable optical response of the metal complex in response to illumination is detected qualitatively, or optionally quantitatively. The detectable optical response of the metal complex is typically a long-lifetime luminescence response.

The optical response is typically detected by means that include visual inspection, CCD cameras, video cameras, photographic film, or the use of currently used instrumentation such as laser scanning devices, fluorometers, photodiodes, quantum counters, epifluorescence microscopes, scanning microscopes, flow cytometers, fluorescence microplate readers, or by means for amplifying the signal such as photomultiplier tubes. When recording the optical response of electrophoretic gels, the use of a film such as POLAROID film results in enhanced sensitivity of signal versus purely visual observation. The metal complex of the invention typically has an emission near 610–630 nm for ruthenium complexes, 650–670 nm for binuclear ruthenium complexes, and 560–580 nm for rhenium complexes, although selection of an appropriate nitrogen donor ligand can be used to modify both the absorption and emission wavelengths somewhat. The sensitivity of detection is improved by use of techniques that permit separation of the poly(amino acids) on very thin gels or in microtube capillaries. The detection limits may also be improved if the medium is illuminated by a stronger light such as a laser, detected with a more sensitive detector, or background signals are reduced via detection of delayed luminescence. The high Stokes shifts of the metal complexes of the present invention result in an excellent signal-to-noise ratio by decreasing the contribution of scattered light and endogenous fluorescence to the background.

The presence of luminescence is optionally used to identify the presence of poly(amino acids) in the test sample. Alternatively, the detectable optical response is quantified and used to measure the concentration of the poly(amino acid) in the test sample mixture. Quantification is typically performed by comparison of the optical response to a prepared standard or to a calibration curve. Typically, the measured optical response is compared with that obtained from a standard dilution of a known concentration of a poly(amino acid) or poly(amino acid) mixture in an electrophoretic gel, or on a membrane. Generally a standard curve must be prepared whenever an accurate measurement is desired. Alternatively, the standard curve is generated by comparison with a reference dye or dyed particle that has been standardized versus the metal complex-stained poly(amino acids).

Stained electrophoretic gels are used to analyze the composition of complex sample mixtures and additionally to determine the relative amount of a particular poly(amino acid) in such mixtures. Stained gels are also used to estimate the purity of isolated proteins and to determine the degree of proteolytic degradation of poly(amino acids) in the sample mixture. In addition, electrophoretic mobility is optionally used to provide a measure of the size of uncharacterized poly(amino acids) and to analyze subunit composition for multi-subunit proteins, as well as to determine the stoichiometry for subunits bound in such proteins. In the case of isoelectric focusing electrophoresis (IEF), electrophoretic mobility is used to provide a measure of the net molecular charge possessed by the poly(amino acid).

The use of the complexes of the invention provides higher sensitivity poly(amino acid) detection than other comparable electrophoresis gel stains, and can be used with both ultraviolet and with visible light excitation. In one aspect of the invention, the instant method is utilized with automated electrophoresis methods. Using the instant method, the bright luminescence of even small amounts of poly(amino acids) permits their detection by automated imaging systems. Further, unlike many electrophoretic gel stains, the instant method incorporates 'endpoint staining'. That is, while an electrophoretic gel may be compromised by silver staining beyond the optimum end point, gels stained using the instant method do not suffer from prolonged staining, and in some formulations do not require destaining, further simplifying the use of automated staining systems. The sensitivity and bright luminescence of the instant metal complexes facilitate the accurate localization of poly(amino acid) bands or spots by automatic systems, permitting their subsequent transfer and/or analysis.

In one aspect of the invention, the localization of poly (amino acid) bands or spots further comprises the physical removal of the bands or spots, followed by separation of the poly(amino acids) from the electrophoretic matrix. In another aspect of the invention, the localization of poly (amino acid) bands or spots further comprises ionization of the poly(amino acids) and characterization by mass spectroscopy (Example 22), or transfer and subsequent analysis of the poly(amino acids) by Edman sequencing (Example 21).

The instant metal complexes have demonstrated utility as a single color viability stain when used in conjunction with flow cytometry or luminescence imaging. While not wishing to be bound by theory, it appears that nonviable cells (having compromised cell membranes) offer greater accessibility of the amines present in cellular proteins to the metal complex, resulting in enhanced luminescence relative to stained viable cells (as in Example 20).

Due to the simplicity of use of the instant metal complexes, they are particularly useful in the formulation of a kit for the labeling of poly(amino acids), comprising one or more metal complexes (preferably in a stock solution), instructions for the use of the metal complex to stain or detect poly(amino acids), and optionally comprising poly (amino acid) standards and other components (such as buffers or wash solutions). In one embodiment, the kit of the invention comprises an aqueous stock solution of a metal complex of the invention and one or more additional kit components.

The additional kit components optionally include acids, buffering agents, inorganic salts, polar solvents, antioxidants, or metal chelators. The additional kit components are present as pure compositions, or as aqueous solutions that incorporate one or more additional kit components. Any or all of the kit components optionally further comprise buffers. Where the kit component is an acid, it is optionally phosphoric acid, acetic acid, or trichloroacetic acid. Where the additional kit component is a polar solvent, it is typically a lower alcohol such as methanol or ethanol, or a diol having 2–6 carbon atoms. Where the additional kit component is an inorganic salt, it is typically an ammonium or magnesium salt.

The examples below are given so as to illustrate the practice of this invention. They are not intended to limit or define the entire scope of this invention.

EXAMPLES

Example 1

Visualization of Protein Dot-blotted or Slot-blotted to Nitrocellulose Membrane

A serial dilution of the protein of interest is prepared in distilled and deionized water (dd-$H_2O$) or other suitable solution such as 7% acetic acid or 20 mM Tris HCl, pH 6.8, 500 mM NaCl. For dot-blotting, 1–5 µL volumes of the protein sample are applied to a 0.4 µm pore size nitrocellulose membrane using a pipetter. Slot-blotting is performed using a Bio-Dot SF vacuum apparatus (Bio-Rad Laboratorifes, Hercules, Calif.). For slot-blotting, membranes are rehydrated with 100 µL/well dd-$H_2O$, samples are applied to the membranes (200 µL/well), wells are rinsed twice with 600 µL of 7% acetic acid/10% methanol and twice with 600 µL of dd-$H_2O$. Following dot- or slot-blotting, membranes are allowed to air dry to minimize loss of protein during subsequent staining steps. The membrane is incubated for 5 minutes each in four changes of dd-$H_2O$. The membrane is completely immersed in 7% acetic acid, 10% methanol, 0.5 µM Compound 3 for 15–30 minutes. The membrane is washed 4–6 times for 1 minute each in dd-$H_2O$. This serves to remove excess dye from the membrane. The membrane is allowed to air dry and is subsequently viewed using a reflective or transmissive 300 nm UV light source. Spotted proteins appear as red to orange luminescent bands on a faint pink to faint blue background. By comparison, staining proteins on nitrocellulose membranes with Coomassie blue dye by standard methods requires lengthy destaining of the membrane in 7% acetic acid/10% methanol for adequate visualization of proteins.

Example 2

Visualization of Protein Electroblotted to Nitrocellulose Membrane

Proteins of interest are separated by SDS-polyacrylamide gel electrophoresis and transferred to nitrocellulose membrane using standard procedures. The membrane is allowed to air dry and is stained in 7% acetic acid, 10% methanol, 0.5 µM Compound 4 as described in Example 1 for slot-blotted proteins. The membrane is allowed to air dry and is subsequently viewed using a reflective or transmissive 300 nm UV light source. This procedure is also appropriate for poly(vinylidene difluoride) membrane as long as the dry membrane is rehydrated with methanol or other suitable organic solvent prior to electroblotting and staining. Proteins appear as red to orange luminescent bands on a very faint pink background. Compared with other staining procedures for electroblotted proteins, Compound 4 has several advantages in terms of sensitivity and compatibility with immunoblotting (see Table 3).

TABLE 3

Comparison of different stains for the detection of electroblotted proteins.

| Stain | Sensitivity[1] (ng/band) | Membranes commonly stained | Reversible?[2] | Compatible with immuno-blotting?[3] | Compatible with Edman sequencing?[4] | Compatible with mass spectrometry?[5] |
|---|---|---|---|---|---|---|
| Colloidal gold | 2–4 | PVDF, nitrocellulose | No | No | No | No |
| Compound 1 | 2–8 | PVDF, nitrocellulose | No | Yes | Yes | Yes |
| India Ink | 4–8 | PVDF, nitrocellulose | No | No | No | No |
| Coomassie Brilliant Blue R-250 | 10–30 | PVDF | No | No | Yes | Yes |
| SYPRO ® Rose dye | 15–30 | PVDF, nitrocellulose | Yes | Yes | not determined | Yes |
| colloidal silver | 15–30 | PVDF, nitrocellulose | No | not determined | not determined | Yes |
| Amido Black | 15–60 | PVDF, nitrocellulose | No | No | Yes | Yes |
| Ferrozine/ferrous | 15–100 | PVDF, nitrocellulose | Yes | Yes | Yes | Yes |
| Fast Green FC | 15–100 | PVDF, nitrocellulose | No | No | Yes | Yes |
| Congo Red | 30–60 | PVDF, nitrocellulose | No | not determined | not determined | not determined |
| Ponceau S | 60–100 | nitrocellulose | Yes | Yes | Yes | Yes |

[1]Note that typically only 50–70% of the protein applied to a polyacrylamide gel is subsequently transferred to the blotting membrane. Sensitivity values are given in terms of actual amount of protein loaded on the gel prior to electrotransfer.
[2]By reversible is meant that staining is removed by change in pH or inclusion of an organic solvent such as methanol.
[3]Staining does not interfere with subsequent immunoblotting techniques well-known in the art
[4]Staining does not interfere with subsequent characterization by Edman Degradation using techniques well-known in the art
[5]Staining does not interfere with subsequent characterization by mass spectrometry using techniques well-known in the art Example 3

Visualization of Protein Electroblotted to Poly (vinylidene difluoride) Membrane Without Rehydrating Proteins of interest are separated by SDS-polyacrylamide gel electrophoresis and transferred to poly(vinylidene difluoride) membrane that has first been rehydrated with methanol using standard procedures. The membrane is allowed to air dry. Since poly(vinylidene difluoride) membrane is not rehydrated in aqueous solutions without prior treatment with an organic solvent such as methanol, the membrane is now refractory to wetting. The membrane is floated face down in 7% acetic acid, 10% methanol, 0.5 $\mu$M Compound 5 for 15–30 minutes. The membrane is floated face down in dd-H$_2$O and incubated for 1 minute. This serves to remove excess dye from the membrane. The membrane is allowed to air dry and is subsequently viewed on a 300 nm UV light box. Background staining is greatly reduced compared with example 2, due to the refractory nature of the unwetted membrane. Proteins appear as red to orange luminescent bands on a very faint pink background.

Example 4

Detection of Protein in Filtration Plates by Standard or Time-resolved Luminescence Prior to protein application the hydrophobic membranes in individual wells of a 96-well Millipore MultiScreen filtration plate are wetted with methanol and then rinsed with 7% acetic acid using a vacuum manifold per manufacturer's instructions (Millipore Corporation, Bedford, Mass.). 0.2 to 1000 ng/mm$^2$ of bovine serum albumin is applied to individual wells without application of a vacuum. The plate is incubated for 30–60 minutes before protein is removed by application of a vacuum. The filtration plate is then allowed to air dry and wells are incubated in 200 $\mu$L of 7% acetic acid, 10% methanol, 1.5 $\mu$M Compound 1 for 15–30 minutes without prior rehydration of the membrane with methanol or similar organic solvent. The dye solution is removed from the wells by pipetting and 200 $\mu$L of 7% acetic acid is applied and removed by pipetter 3–4 times to remove any unbound dye. The filtration plate is subsequently read using a Perkin-Elmer HTS 7000 microplate reader or similar device. An excitation filter of 485 nm and an emission filter of 595 nm is selected. Measurements are made through the top face of the plate. Gain is set to 60 and flashes are used per well Integration time is set to 20 $\mu$seconds. For time-resolved luminescence, all instrument parameters are maintained except that integration of signal begins 10 $\mu$second after a flash of light and integration time is increased to 100 $\mu$seconds. Instrument software provides digital values corresponding to the luminescence intensity of the signal from the dye in each well.

Example 5

Visualization of Proteins Resolved by Carrier Ampholyte-mediated Isoelectric Focusing Gel Electrophoresis Isoelectric focusing (IEF) can be performed utilizing a variety of pre-cast and laboratory prepared gels that employ different chemistries to generate a pH gradient. In this instance, IEF Ready Gels are run vertically for 600 volt-hours using a Mini-Protean II Electrophoresis Cell (BioRad, Hercules, Calif.) according to manufacturer's instructions except that 10 mM phosphoric acid and 100 mM sodium hydroxide are utilized as anode and cathode buffer, respectively. Alternatively, Ampholine PAGplates are run horizontally for 1500 volt-hours using a Multiphor II electrophoresis unit (Amersham-Pharmacia Biotech, Uppsala, Sweden) per manufacturer's instructions. In another alternative, denaturing, 1 mm IEF slab gels are cast utilizing a 4% T, 2.6% C polyacrylamide gel matrix, containing 9 M urea, 2% Triton X-100, and 2% carrier ampholytes. % T is the total monomer concentration (acrylamide+crosslinker) expressed in grams per 100 mL and % C is the percentage crosslinker (e.g. N,N-methylene-bis-acrylamide, N,N'-diacryloylpiperazine or other suitable agent). Electrophoresis is performed on a Multiphor II electrophoresis unit for 1500 volt-hours using 10 mM phosphoric acid and 100 mM sodium hydroxide as anode and cathode buffer, respectively. Luminescent staining of gels is performed by fixing gels in 12.5% trichloroacetic acid for one hour, followed by incubation in 12.5% trichloroacetic acid, 25% ethanol, 1.5 μM Compound 1 for 15 hours (overnight). Gels are then rinsed in two changes of water for one hour each and viewed by illumination with a 300 nm UV light source. The polyester backing sheet on Ampholine PAGplates usually separates from the gel during the incubations in water. Since this sheet often has residual dye bound to it, background staining is reduced by removing the sheet from the gel. Proteins appear as red to orange luminescent bands on a clear background. A comparison of IEF gel staining using colloidal Coomassie Blue, Silver staining and Compound 1 is shown in Table 4.

TABLE 4

| Marker Protein | isoelectric point | Sensitivity Limit (ng/band) | | |
|---|---|---|---|---|
| | | Colloidal Coomassie Blue | Silver | Compound 1 |
| amyloglucosidase | 3.50 | 560–1390 | 7–17 | 7–17 |
| soybean trypsin inhibitor | 4.55 | 1670–4160 | 190–460 | 60–150 |
| β-lactoglobulin A | 5.20 | 560–1390 | 1670–4160 | 190–460 |
| bovine carbonic anhydrase B | 5.85 | 1670–4160 | 190–460 | 60–150 |
| human carbonic anhydrase B | 6.55 | 560–1390 | 1670–4160 | 60–150 |
| horse myoglobin, acidic band | 6.85 | 1670–4160 | 190–460 | 190–460 |
| horse myoglobin, basic band | 7.35 | 60–150 | 1670–4160 | 60–150 |
| lentil lectin, acidic band | 8.15 | 560–1390 | 190–460 | 60–150 |
| lentil lectin, middle band | 8.45 | 560–1390 | 190–460 | 190–460 |
| lentil lectin, basic band | 8.65 | 560–1390 | 190–460 | 60–150 |
| trypsinogen | 9.30 | 1670–4160 | 560–1390 | 60–150 |

Example 6

Visualization of Proteins Resolved by Immobilized pH Gradient (IPG) Electrophoresis IPG electrophoresis is performed using pre-cast pH 4–7 Immobiline Dry Plates (Amersham-Pharmacia Biotech, Uppsala, Sweden). Gels are rehydrated in 2% Pharmalyte 3–10 ampholytes using a reswelling cassette according to manufacturer's instructions (Amersham-Pharmacia Biotech, Uppsala, Sweden). Electrophoresis is performed horizontally for 10,000 volt-hours using a Multiphor II electrophoresis unit. After electrophoresis, gels are incubated in 12.5% trichloroacetic acid for one hour, followed by incubation in 12.5% trichloroacetic acid, 25% ethanol, 1.5 μM Compound 4 for 15 hours (overnight). Gels are then rinsed in two changes of water for one hour each and viewed by illumination with a 300 nm UV light source. The polyester backing of the Immobiline gel usually remains bound to the derivatized polyacrylamide. The gel is placed on the UV light source so that the polyester sheet is face up for optimal visualization of the stained protein bands. Proteins appear as red to orange luminescent bands on a very faint pink to faint blue background.

Example 7

Visualization of Proteins Resolved by Sodium Dodecylsulfate Polyacrylamide Gel Electrophoresis (with destaining)

Proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. The gel is subsequently incubated in 25% trichloroacetic acid for 20 minutes, incubated in three changes of 30% methanol for 20 minutes each, and stained in 30% methanol, 1.5 mM Compound 1 for 1–2 hours. Inspection of the gel using a hand held midrange UV light source indicates that the entire gel is stained. The gel is subsequently transferred to a destaining solution of 30% methanol, 7% acetic acid and is incubated for an additional 4–6 hours. At this point dye is eluted from the polyacrylamide matrix but selectively retained on the proteins within the matrix. The gel is viewed using a 300 nm UV transilluminator. Proteins appear as red to orange luminescent bands on a pale pink background.

Example 8

Visualization of Proteins Resolved by Sodium Dodecylsulfate Polyacrylamide Gel Electrophoresis (without destaining)

Proteins of interest are separated by SDS-polyacrylamide gel electrophoresis utilizing a 4% T, 2.6% C stacking gel, pH 6.8 and 15% T, 2.6% C separating gel, pH 8.8 according to standard procedures. After electrophoresis, gels are incubated in 7% ammonium sulfate, 34% methanol, 2% phosphoric acid 1.5 μM Compound 2 for 2–15 hours. Gels are rinsed in dd $H_2O$ for 10–15 minutes and viewed using a 300 nm UV transilluminator. Proteins appear as red to orange luminescent bands on a clear background. Compared to Example 7, this is the preferred method of staining polyacrylamide gels as any destaining step also removes dye from proteins, thus reducing signal. Table 5 compares the sensitivity of some common stains with the colloidal ruthenium complex

TABLE 5

| Detection Reagent | Sensitivity (ng/band) |
|---|---|
| Colloidal Coomassie Blue dye | 8–16 |
| Silver stain | 2–4 |
| SYPRO ® Orange dye | 2–4 |
| Compound 2 | 1–2 |

Example 9

Visualization of Proteins in Non-denaturing Polyacrylamide Gel Electrophoresis

Proteins from mouse 3T3 fibroblasts are homogenized in 0.2% Triton X-100, ultrasonically disrupted with a probe sonicator (3 bursts, 20% power) and centrifuged for 2 minutes at 13,000×g to pellet any particulate matter. The supernate is adjusted to 10% in glycerol, and 80 mM Tris-HCl, pH 6.8. Approximately 100 μg of protein is applied to each lane of a polyacrylamide gel that consists of a 4% T, 2.6% C stacking gel, pH 6.8 and 7% T, 2.6% C separating gel, pH 8.8. The gels and buffers are prepared according to standard procedures except that sodium dodecyl sulfate and reducing agent (e.g. dithiothreitol or 2-mercaptoethanol) are omitted from all components. Electrophoresis is performed according to standard procedures using a 25 mM Tris, 192 mM glycine, pH 8.8 electrode buffer. After electrophoresis, gels are incubated in 7% ammonium sulfate, 34% methanol, 2% phosphoric acid 1.5 μM Compound 1 for 1–15 hours. Gels are rinsed in dd $H_2O$ for 10–15 minutes and viewed using a 300 nm UV transilluminator. Proteins appear as red to orange luminescent bands on a clear background.

Example 10

Visualization of Proteins Resolved by Two-dimensional Gel Electrophoresis

A mouse 3T3 fibroblast cell lysate protein mixture is solubilized in 8 M urea, 2% Triton X-100, 2% carrier ampholytes, 100 mM dithiothreitol, 0.1% sodium dodecyl sulfate, 12.5 mM Tris, pH 8.0. Approximately 50 μg of protein is applied to 1 mm diameter, 20 cm long isoelectric focusing gels consisting of a 4% T, 2.6% C polyacrylamide gel matrix, containing 9 M urea, 2% Triton X-100, and 2% carrier ampholytes. Gels are run vertically for 18,000 volt-hours using 10 mM phosphoric acid and 100 mM sodium hydroxide as anode and cathode buffer, respectively. Isoelectric focusing gels are incubated in 0.3 M Tris base, 0.075 M Tris-HCl, 3% SDS, 0.01% bromophenol blue for two minutes. Isoelectric focusing gels are then laid on top of 1 mm thick, 20 cm×20 cm, 12.5% T, 2.6% C polyacrylamide gels containing 375 mM Tris-base, pH 8.8 and SDS-polyacrylamide gel electrophoresis is performed according to standard procedures except that the cathode electrode buffer is 50 mM Tris, 384 mM glycine, 4% sodium dodecyl sulfate, pH 8.8 while the anode electrode buffer is 25 mM Tris, 192 mM glycine, 2% sodium dodecyl sulfate, pH 8.8. After the second dimension electrophoresis, gels are incubated in approximately 500 mL of 34% methanol, 2% phosphoric acid for 1 hour. Gels are subsequently incubated for 15 hours in 12.5% trichloroacetic acid, 25% methanol, 1.5 μM Compound 1. Gels are rinsed in dd $H_2O$ for 10–15 minutes and viewed using a 300 nm UV transilluminator. Proteins appear as red to orange luminescent spots on a clear background.

Example 11

Visualization of Latent Fingerprints on Solid Substrata

A thumb or finger is firmly pressed against a dry glass microscope slide, nitrocellulose or poly(vinylidene difluoride) membrane (substrata). The substrata is then incubated in 7% acetic acid, 2.5 μM Compound 1 for 15–30 minutes, incubated in dd-$H_2O$ for 5 minutes and allowed to air dry. The substrata is then viewed with a hand held UVM-57 midrange UV-302 nm lamp (UVP, Inc. Upland, Calif.). Fingerprints appear as red to orange luminescent patterns on a very faint pink background.

Example 12

Detection of Proteins in Gels or on Membranes Using a Laser-excited Gel Scanner

Proteins on membranes or in polyacrylamide gels are stained as described in examples 1–3 or 5–10, respectively. Stained material is placed in a laser-excited gel scanner such as a Molecular Devices FLUORIMAGER, Molecular Devices STORM (Molecular Devices, Sunnyvale, Calif.), or Hitachi FMBIO II (Hitachi, San Bruno, Calif.) instrument. For the FLUORIMAGER scanner, excitation is achieved with a 488 nm argon-ion laser source and a 610+/−15 nm emission filter is utilized to collect signal. For a STORM scanner, blue fluorescence mode is used which corresponds to 450+/−30 nm excitation and a 520 nm long pass filter is used to collect signal. For a Hitachi FMBIO II instrument, excitation is achieved using a 532 nm frequency-doubled YAG laser and signal is collected utilizing 585, 605, 625 or 650 nm emission filters. Proteins appear as white bands on a gray to black background or as black bands on light gray to white background on the computer monitor depending upon the display mode selected. Instrument software provides digital values corresponding to the fluorescence intensity of the signal in each band.

Example 13

Detection of Proteins in Gels by Photography

Proteins on membranes or in polyacrylamide gels are stained as described in examples 1–3 or 5–10, respectively. Stained material is placed on a 300 nm UV-transilluminator. The stained proteins in the gel are photographed using Polaroid 667 black and white print film using a Kodak #Wratten 9 gelatin filter. Proteins appear as white bands on a gray to black background in the Polaroid photograph.

Example 14

Detection of Proteins in Gels Using a CCD Camera Scanner

Proteins on membranes or in polyacrylamide gels are stained as described in examples 1–3 or 5–10, respectively. Stained material is placed on the UV-transilluminator of a CCD camera-based imaging workstation such as a Boehringer-Mannheim Lumi-Imager (Boehringer-Mannheim, Indianapolis, Ind.), Genomic Solutions Biolmage (Genomic Solutions, Ann Arbor, Mich.) or Bio-Rad Fluor-S system (Bio-Rad, Hercules, Calif.). All units provide excitation illumination of about 300 nm. 600+/−30 nm band pass emission filters are used with the Lumi-Imager and BioImage systems while a 520 nm long pass emission filter is used with the Fluor-S. Images of gels are captured utilizing standard software-driven procedures provided by each manufacturer. Proteins appear as white bands on a gray to black background or as black bands on light gray to white background on the computer monitor depending upon the display mode selected. Instrument software provides digital values corresponding to the fluorescence intensity of the signal in each band.

Example 15

Visualization of Proteins Using a Fluorescent Blue Light Source

Proteins on membranes or in polyacrylamide gels are stained as described in examples 1–3 or 5–10, respectively. Stained material is placed on a blue light box, such as a DARK READER (Clare Chemical Research, Denver, Colo.) equipped with a 9 watt blue fluorescent bulb (e.g. Sylvania DuLux CF9DS/Blue, Osram-Sylvania, Waltham, Mass.). With this instrument, gels are viewed in a darkened room. The stained gel is placed on the DARK READER and an amber sheet of plastic (supplied with the device) is placed on top of the gel. Proteins appear as red to orange luminescent bands on a dark background.

Example 16

Visualization of Tissue Prints

The tips of green onion shoots are cut as close to the end as possible to expose the meristematic region. The cut ends of the plant are pressed lightly against the nitrocellulose surface of a Grace Bio-Labs ONCYTE film slide for 15 to 120 seconds (Grace BioLabs, Bend, Oreg.). The slide is allowed to air dry for one hour and the slide is fixed in 3.7% paraformaldehyde in TBS (100 mM Tris-base, 150 mM NaCl, pH 7.5) using a humidified chamber. The slide is washed three times for 15 minutes each in TBS and then twice more with dd-$H_2O$. The slide is stained for 15 minutes in 5 mM Compound 1, 7% acetic acid in a humidified chamber. The slide is subsequently washed twice in dd-$H_2O$. Tissue prints are viewed on a standard 300 nm UV light box or with a Nikon fluorescence microscope using 480+/−30 nm excitation and 635+/−28 nm emission filters. Tissue is easily visualized as red-to orange luminescent regions on a dark background.

Example 17

Staining Fixed Mammalian Cells

ROS 17.1 osteosarcoma cells (American Type Culture Collection (ATCC), Manassas, Va.) are grown on glass cover slips and fixed in 3.7% formaldehyde in 100 mM Tris-base, 150 mM NaCl, pH 7.5 by standard procedures. Fixed cells are rinsed 3 times in 2.7 mM KCl, 1.5 mM $KH_2PO_4$, 136 mM NaCl, 8.1 mM $Na_2HPO_4$, pH 7.0 (phosphate-buffered saline). Cover slips are incubated in 5 $\mu$M Compound 1, 7% acetic acid for 10 minutes and then washed twice with dd-$H_2O$. Cells are viewed with a Nikon fluorescence microscope using a 480+/−30 nm excitation filter and 635+/−28 nm emission filter. Cells appear as red-to-orange luminescent regions on a dark background. The dye stains the entire cell but appears concentrated in the nucleus, excluding the nucleolus, with extra staining observed in the coiled bodies.

Example 18

Lack of Labeling of DNA in Polyacrylamide Gels

A dilution series of DNA molecular weight marker IX (Boehringer-Mannheim, Indianapolis, Ind.) ranging from 250 nanograms to 30.5 picograms total double stranded DNA is applied to a 5% T, 5% C polyacrylamide gel and electrophoretically separated by standard procedures. After electrophoresis, gels are incubated for 15 hours in 34% methanol, 2% phosphoric acid, 7% ammonium sulfate, 1.5 $\mu$M Compound 1. Subsequently, gels are placed on a 300 nm UV transilluminator to visualize DNA bands. No luminescent bands are observed, indicating that the staining procedure preferentially visualizes proteins.

Example 19

Visualization of Amino Acid Homo- and Heteropolymers on Nitrocellulose Membrane Homopolymers of poly-L-arginine, asparagine, histidine, lysine, apartate, glutamate, alanine, glycine, isoleucine, leucine, methionine, serine, threonine, tryptophan, tyrosine and proline are prepared at a concentration of 1 $\mu$g/mL. The amino acid heteropolymers, poly(glutamate, alanine, tyrosine), poly(glutamate, tyrosine), poly(lysine, tyrosine), poly(glutamate, lysine, tyrosine), and poly(arginine, tyrosine) are prepared in an identical manner as the homopolymers. All polymers are obtained from Sigma Chemical Company (St. Louis, Mo.). 1–5 $\mu$L volumes of the polymers are applied to a nitrocellulose membrane and allowed to air dry. Staining is performed according to Example 1, using a dye of the invention. Only select polymers are noted to stain with the dye as demonstrated by strong orange to red luminescence. The dye is observed to interact primarily with polymers containing the basic amino acids; histidine, lysine or arginine. Weak reactivity with tryptophan and tyrosine is also observed.

Example 20

Staining Peptides After Separation by Thin-layer Chromatography

Two peptides, Kemptide (a 7-mer) and Dinorphin A (a 15-mer), are dissolved to a final concentration of 1 mg/mL in water. Approximately 1 microliter of peptide solution is spotted onto a dry, silica thin-layer chromatography plate. The spotted peptides are subjected to thin-layer chromatography eluting with 1-butanol:acetic acid:pyridine:water (37.5:7.5:25:30) using standard procedures. After the solvent front runs about two-thirds the length of the TLC plate, the plate is removed from solvent and allowed to air dry. The plate is then immersed in 10% methanol, 7% acetic acid for 15 minutes. The plate is subsequently immersed in a solution that is 5 $\mu$M Compound 1 in 10% methanol, 7% acetic acid for 15 minutes. The plate is washed in three changes of dd-$H_2O$ and allowed to air dry. The plate is visualized with a hand held 300 nm UV light source. The chromatographed peptides appear as red to orange luminescent spots on a very faint pink background.

Example 21

Edman Sequencing of Proteins Electroblotted to Transfer Membranes

Proteins of interest are subjected to electrophoresis, subsequently transferred to poly (vinylidene difluoride) membranes and stained as described in Example 3. After the target proteins are identified, the bands are excised with a sharp razor. The excised bands are then either used directly or incubated in 150 mM Tris, pH 8.8, 20% methanol for 30 minutes and rinsed in 3 changes of deionized water. The Tris/methanol incubation partially destains the proteins, thus removing excess dye. For internal protein sequencing, the target proteins are excised from the nitrocellulose membrane, subjected to in situ proteolytic cleavage, for 3 hours at 37° C., and in the presence of 10% acetonitrile, 3% Tween-80 in 100 mM ammonium bicarbonate, pH 8.3. Resulting fragments are then separated by micro-bore reverse phase HPLC. Selected peak fractions are analyzed by automated Edman degradation. Proteins subjected to Edman sequencing without destaining exhibited low initial and repetitive sequencing yields. The partially destained proteins, however, produce high quality spectra with excellent initial and repetitive sequencing yields.

Example 22

Matrix-assisted Laser Desorption Mass Spectrometry-based

Proteins of interest are subjected to electrophoresis, subsequently transferred to poly (vinylidene difluoride) membranes and stained as described in Example 3. After target proteins are identified, the bands are excised with a sharp razor. The selected bands are then washed 3 times 5 minutes in 25 mM ammonium bicarbonate pH 7.8, 10% methanol and allowed to dry. After drying, the bands are cut into 1–2 mm squares and incubated in 20 μg/ml trypsin in digest buffer (25 mM ammonium bicarbonate, pH 7.8 with 1% octyl β-glucoside and 10% methanol added). Sufficient volume of the trypsin digestion mixture is added to cover the membrane squares. Proteins are digested at room temperature for 5–6 hours and then incubated overnight at 27–28° C. The peptides are extracted with formic acid:ethanol, (1:1) and then lyophilized. After lyophilization, the peptides are resuspended in water for analysis by matrix assisted laser desorption ionization mass spectrometry (MALDI-MS). Equal volumes of the peptide digests are mixed with α-cyano-4-hydroxycinnamic acid matrix (10 mg/ml in 70% acetonitrile/$H_2O$). The mixture is spotted onto the sample plate and air dried prior to analysis. MALDI-MS analysis is performed using a Voyager Mass Spectrometer, (PerSeptive BioSystems, Framingham, Mass., USA). The instrument is calibrated with Substance-P (1347.7 Da) and insulin (5731.4 Da). The peptide masses obtained from the trypsinized protein are used to search the EMBL peptide database using the PeptideSearch engine available on the world wide web, (www.mann.embl-heidelberg.de). Proteins are readily identified with good peptide sequence coverage.

Example 23

Differentiating Live and Dead Cells by Flow Cytometry

Jurkat cells obtained from American Type Culture Collection Co., Manassas, Va. are used. They are grown in suspension in RPMI 1640 medium supplemented with 10% fetal calf serum, 2 mM L-glutamine, 100 U/mL penicillin and 100 μg/mL streptomycin. The jurkat cells are centrifuged, and the cell pellet collected. The cell pellet is washed once with phosphate buffered saline (PBS; pH 7.2), and resuspended in 1000 μL of PBS. An aliquot of 250 μL of this cell suspension is placed in an ice bath, while another 250 μL of the cell suspension is placed in a glass test-tube and incubated in a water bath at 60° C. After 10–15 minutes, the test-tube is removed from the water bath. To a microcentrifuge tube containing 900 μL of PBS is added 5 μL of a 1 mL solution of Compound 1. A combined suspension of 50 μL of the heat-treated (dead) cell suspension and 150 μL of the live cell suspension is prepared, and 100 μL of the mixed cell suspension is added drop-wise to the dye solution. To another tube containing 900 μL of PBS is added 100 μL of the mixed cell suspension drop-wise. Each suspension is incubated on ice for 3 minutes, microcentrifuged, washed twice with PBS and re-suspended in the same. Each group of cells is then transferred to a separate flow cytometer tube. To the unstained is added a 5 μM solution of the dead cell stains SYTOX GREEN stain (Molecular Probes, Inc.) to a final concentration of 0.5 nM.

The cell suspensions are analyzed by flow cytometry: Data acquisition is performed using a Becton-Dickinson FACS Vantage flow cytometer (San Jose, Calif.). The 488-nm line of an air-cooled argon-ion laser is used at 100 mW. Sample acquisition and analysis are performed using CellQuest version 1.2 software. The photomultiplier tubes (PMT) used for detecting green fluorescence (SYTOX GREEN stain) is equipped with a 530±15 nm emission filter and for detecting red luminescence (Compound 1) a 630±11 nm filter is used. After analysis is complete, additional SYTOX GREEN stain is added to the cell sample stained with Compound 1, to a final concentration of 0.5 nM, and the sample is analyzed again.

Heat treated (dead) cells stained with Compound 1 exhibit approximately 10-fold brighter luminescent staining than stained live cells, permitting easy differentiation of dead cells. The sample stained with both Compound 1 and SYTOX GREEN stain exhibits coincident green and red fluorescence, verifying that preferential staining of dead cells is occurring.

When the experiment is repeated using prepared mixtures of heat-killed and live cells in varying proportions so that the percentage of dead cells in the mixtures is 0, 10, 25, 50, 75, 90 and 100%, respectively. The mixtures are prepared in a 100 μL volume, stained with Compound 1 and analyzed by flow cytometry as above. Flow cytometric analysis of the mixtures shows measured dead cell percentages of 2, 13, 31, 46, 65, 76 and 96% respectively.

It is to be understood that, while the foregoing invention has been described in detail by way of illustration and example, numerous modifications, substitutions, and alterations are possible without departing from the spirit and scope of the invention as described in the following claims.

What is claimed is:

1. A method, comprising:
   a) combining a sample mixture that is thought to contain a poly(amino acid) with a staining mixture that contains one or more metal complexes to form a combined mixture;
      wherein each metal complex, which may be the same or different, comprises one or more transition metal ions of Group 7, Group 8, Group 9, or Group 10, said metal ion having an atomic number greater than 42, and having a plurality of nitrogen donor ligands fully coordinated thereto, wherein each nitrogen donor ligand, which may be the same or different, comprises at least one heteroaromatic ring containing a nitrogen atom, provided that at least one of said nitrogen donor ligands is substituted by at least one anionic moiety; and
      further provided that said metal complex is neutral or anionic in overall electronic charge;
   b) incubating the combined mixture for a time sufficient for said metal complex to associate with the poly (amino acid) to form a stained poly(amino acid) complex that gives a detectable optical response upon illumination;
   c) illuminating said dye-poly(amino acid) complex; and
   d) observing said detectable optical response.

2. A method, as claimed in claim 1, wherein the staining mixture each anionic moiety is independently selected from phosphate, thiophosphate, phosphonate, carboxylate, boronate, sulfate, sulfonate, thiosulfate, and thiosulfonate, or a salt thereof.

3. A method, as claimed in claim 1, wherein in the staining mixture each anionic moiety is sulfonate or a salt thereof.

4. A method, as claimed in claim 1, wherein in the staining mixture at least one metal ion is a ruthenium, an osmium, a rhenium, or a platinum ion.

5. A method, as claimed in claim 4, wherein the metal ion is monocationic or dicationic.

6. A method, as claimed in claim 1, wherein in the staining mixutre at least one metal ion is a ruthenium (II) or rhenium (I) ion.

7. A method, as claimed in claim 1, wherein in the staining mixture, said heteroaromatic rings that contain a nitrogen atom also optionally incorporate one or more additional heteroatoms, which may be the same or different, that are N, O, or S; and said heteroaromatic rings are optionally substituted by halogen; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; aryl; heteroaryl; or one or more additional fused aromatic rings.

8. A method, as claimed in claim 1, wherein in the staining mixture said nitrogen donor ligands, which may be the same or different, are substituted or unsubstituted bipyridyls, bis-pyridyls, phenanthrolines, or ter-pyridyls.

9. A method, as claimed in claim 1, wherein in the staining mixture at least one nitrogen donor ligand has the formula

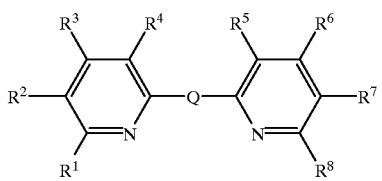

wherein substituents $R^1$, $R^2$, $R^3$, $R^4$, $R^5$, $R^6$, $R^7$, and $R^8$ are independently selected from hydrogen; halogen; an anionic moiety; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; aryl; heteroaryl; or any two adjacent substituents of $R^1$, $R^2$, $R^3$, $R^4$, $R^5$, $R^6$, $R^7$, and $R^8$ when taken in combination form an additional fused aromatic ring that is optionally substituted by halogen; an anionic moiety; cyano; alkyl, perfluoroalkyl, or alkoxy, each having 1–6 carbons; amino; alkylamino having 1–6 carbons; dialkylamino having 2–12 carbons; carboxy; or carboxyalkyl, carboxyalkoxy, carboxyalkylamino, or carboxyalkylthio, each having 2–7 carbons;

wherein each aryl or heteroaryl is optionally and independently substituted by hydrogen, halogen; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; or an anionic moiety;

Q is a single covalent bond; or Q is a formal single bond, and $R^4$ and $R^5$ when taken in combination are $-CR^9=CR^{10}-$; or Q is $-(CR^{11}{}_2)_a-X_b-(CR^{12}{}_2)_c-$, where a, b and c are each 0 or 1; or Q is a 2,6-disubstituted pyridyl;

wherein $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbon atoms; a carboxy; or carboxyalkyl, carboxyalkoxy, carboxyalkylamino or carboxyalkylthio having 2–7 carbon atoms; an aryl or heteroaryl; halogen; CN; or an anionic moiety $R^{11}$ and $R^{12}$ are independently H or alkyl having 1–6 carbon atoms;

X is optionally O, S, $NR^{13}$, or $-CR^{14}R^{15}-$;

where $R^{13}$ is H, $C_1-C_6$ alkyl, or phenyl that is optionally further substituted one or more times in any combination by alkyl, perfluoroalkyl, or alkoxy having 1–6 carbon atoms; an anionic moiety; amino, alkylamino or dialkylamino, where each alkyl group has 1–6 carbon atoms; carboxy; carboxyalkyl, carboxyalkoxy, carboxyalkylamino or carboxyalkylthio having 2–7 carbon atoms; halogen, or CN; and $R^{14}$ and $R^{15}$ are independently H, alkyl having 1–6 carbon atoms, or an anionic moiety;

said 2,6-disubstituted pyridyl is optionally further substituted by alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons; or halogen;

provided that said nitrogen donor ligand is substituted directly or indirectly by at least one anionic moiety that is phosphate, thiophosphate, phosphonate, carboxylate, boronate, sulfate, sulfonate, thiosulfate, and thiosulfonate, or a salt thereof.

10. A method, as claimed in claim 9, wherein said nitrogen donor ligand has the formula

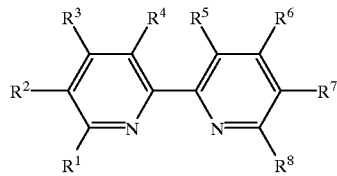

where $R^1-R^8$ are as defined previously, and each anionic moiety is sulfonate or a salt thereof.

11. A method, as claimed in claim 9, wherein said nitrogen donor ligand has the formula

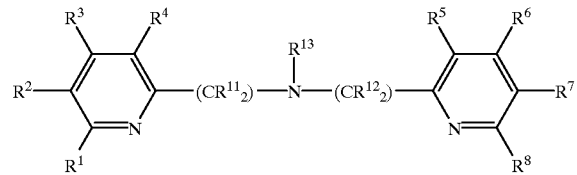

where $R^1-R^8$, $R^{11}$, $R^{12}$, and $R^{13}$ are as defined previously, and each anionic moiety is sulfonate or a salt thereof.

12. A method, as claimed in claim 9, wherein said nitrogen donor ligand has the formula

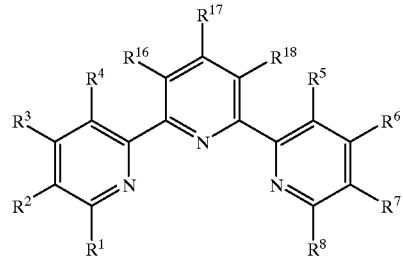

where $R^1-R^4$ and $R^5-R^8$ are as defined previously;

$R^{16}$, $R^{17}$, and $R^{18}$ are independently H; alkyl, perfluoroalkyl, or alkoxy having 1–6 carbon atoms; an anionic moiety; amino, alkylamino or dialkylamino, where each alkyl group has 1–6 carbon atoms; carboxy; or carboxyalkyl, carboxyalkoxy, carboxyalkylamino, or carboxyalkylthio having 2–7 carbon atoms; halogen, or CN; and each anionic moiety is sulfonate or a salt thereof.

13. A method, as claimed in claim 9, wherein said nitrogen donor ligand has the formula

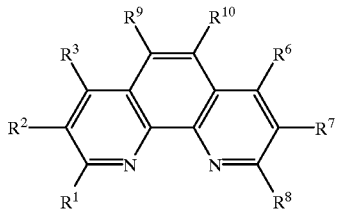

where $R^1$–$R^3$, $R^6$–$R^8$, $R^9$ and $R^{10}$ are as defined previously, and each anionic moiety is sulfonate or a salt thereof.

14. A method, as claimed in claim 13, wherein $R^3$ and $R^6$ are each phenyl that is optionally and independently substituted by at least one sulfonic acid or salt of sulfonic acid.

15. A method, as claimed in claim 1, wherein said detectable optical response is a luminescence response.

16. A method, as claimed in claim 1, further comprising quantitating said poly(amino acid) by measuring said detectable optical response and comparing said measurement with a standard.

17. A method, as claimed in claim 1, wherein the sample mixture is present on or in a solid or semi-solid matrix.

18. A method, as claimed in claim 1, further comprising transferring the sample mixture to a solid or semi-solid matrix before or after combining with the staining mixture.

19. A method, as claimed in claim 1, wherein the sample mixture is present on or in an electrophoresis medium.

20. A method, as claimed in claim 1, further comprising electrophoretically separating the sample mixture before or while it is combined with the staining mixture.

21. A method, as claimed in claim 1, further comprising analyzing the poly(amino acid) by mass spectroscopy.

22. A method, as claimed in claim 1, further comprising analyzing the poly(amino acid) by Edman sequencing.

23. A method, as claimed in claim 1, further comprising adding an additional reagent to the sample mixture, the staining mixture, or the combined mixture.

24. A method, as claimed in claim 20, wherein the electrophoretic separation, the illuminating step, or the observing step is accomplished by automated methods.

25. A method, as claimed in claim 1, further comprising physically separating the components of the sample mixture before or while it is combined with the staining mixture.

26. A method, as claimed in claim 25, wherein said separating step is accomplished by flow cytometric methods, electrophoretic methods, or microfluidic methods.

27. A method, as claimed in claim 25, wherein said sample mixture comprises cells, said separating step is accomplished by flow cytometric methods, and the detectable optical response is correlated to cell viability.

28. A solution comprising:

a metal complex, comprising a transition metal ion that is a ruthenium (II) or a rhenium (I) ion, and 2–3 nitrogen donor ligands fully coordinated thereto, each of said nitrogen donor ligands independently having the formula

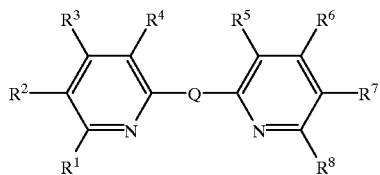

wherein substituents $R^1, R^2, R^3, R^4, R^5, R^6, R^7$, and $R^8$ are independently selected from hydrogen; halogen; an anionic moiety; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; aryl; heteroaryl; or any two adjacent substituents of $R^1, R^2, R^3, R^4, R^5, R^6, R^7$, and $R^8$ when taken in combination form an additional fused aromatic ring that is optionally substituted by halogen; an anionic moiety; cyano; alkyl, perfluoroalkyl, or alkoxy, each having 1–6 carbons; amino; alkylamino having 1–6 carbons; dialkylamino having 2–12 carbons; carboxy; or carboxyalkyl, carboxyalkoxy, carboxyalkylamino, or carboxyalkylthio, each having 2–7 carbons;

wherein each aryl or heteroaryl is optionally and independently substituted by hydrogen, halogen; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; or an anionic moiety;

Q is a single covalent bond; or Q is a formal single bond, and $R^4$ and $R^5$ when taken in combination are —$CR^9$=$CR^{10}$—; or Q is —$(CR^{11}{}_2)_a$—$X_b$—$(CR^{12}{}_2)_c$—, where a, b and c are each 0 or 1; or Q is a 2,6-disubstituted pyridyl;

wherein $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbon atoms; a carboxy; or carboxyalkyl, carboxyalkoxy, carboxyalkylamino or carboxyalkylthio having 2–7 carbon atoms; an aryl or heteroaryl; halogen; CN; or an anionic moiety $R^{11}$ and $R^{12}$ are independently H or alkyl having 1–6 carbon atoms;

X is optionally O, S, $NR^{13}$, or —$CR^{14}R^{15}$—;

where $R^{13}$ is H, $C_1$-$C_6$ alkyl, or phenyl that is optionally further substituted one or more times in any combination by alkyl, perfluoroalkyl, or alkoxy having 1–6 carbon atoms; an anionic moiety; amino, alkylamino or dialkylamino, where each alkyl group has 1–6 carbon atoms; carboxy; carboxyalkyl, carboxyalkoxy, carboxyalkylamino or carboxyalkylthio having 2–7 carbon atoms; halogen, or CN; and $R^{14}$ and $R^{15}$ are independently H, alkyl having 1–6 carbon atoms, or an anionic moiety;

said 2,6-disubstituted pyridyl is optionally further substituted by alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons; or halogen;

provided that said nitrogen donor ligand is substituted directly or indirectly by at least one anionic moiety that is phosphate, thiophosphate, phosphonate, carboxylate, boronate, sulfate, sulfonate, thiosulfate, and thiosulfonate, or a salt thereof;

wherein said met al complex is presen t in a concentration of 0.10 μM to 10 μM;

a polar organic solvent a t a concentration of 5–50%; and either an acidic component at a concentration of 1%–20%, or an inorganic salt that is present at a concentration of 1–50%, or both.

29. A solution, as claimed in claim 28, wherein said polar organic solvent is an alcohol having 1–6 carbons, or a diol or a triol having 2–6 carbon atoms.

30. A solution, as claimed in claim 29, wherein said polar organic solvent is methanol, ethanol, 1,2-ethanediol, or 1,2-propanediol at a concentration of 30–40%.

31. A solution, as claimed in claim 28, wherein said acidic component is acetic acid, trichloroacetic acid, perchloric acid, or phosphoric acid at a concentration of 1–20%.

32. A solution, as claimed in claim 28, wherein said acidic component is trichloroacetic acid at a concentration of about 12.5%, and said polar organic solvent is 1,2-propanediol at a concentration of about 25%.

33. A solution, as claimed in claim 28, wherein said inorganic salt is ammonium sulfate or magnesium chloride, present at a concentration of 5–20%.

34. A solution, as claimed in claim 28, wherein said solution is an aqueous solution; said polar organic solvent is methanol, ethanol, 1,2-ethanediol, or 1,2-propanediol at a concentration of 30–40%; said acidic component is acetic acid, trichloroacetic acid, perchloric acid, or phosphoric acid at a concentration of 1–20%; and said inorganic salt is ammonium sulfate or magnesium chloride, present at a concentration of 5–20%.

35. A kit, comprising:

an stock solution of a metal complex, comprising a transition metal ion that is a ruthenium (II) or a rhenium (I) ion, and 2–3 nitrogen donor ligands fully coordinated thereto, each of said nitrogen donor ligands independently having the formula

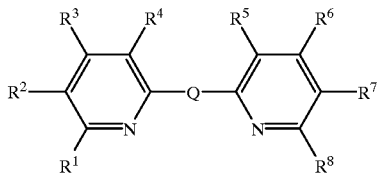

wherein substituents $R^1$, $R^2$, $R^3$, $R^4$, $R^5$, $R^6$, $R^7$, and $R^8$ are independently selected from hydrogen; halogen; an anionic moiety; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; aryl; heteroaryl; or any two adjacent substituents of $R^1$, $R^2$, $R^3$, $R^4$, $R^5$, $R^6$, $R^7$, and $R^8$ when taken in combination form an additional fused aromatic ring that is optionally substituted by halogen; an anionic moiety; cyano; alkyl, perfluoroalkyl, or alkoxy, each having 1–6 carbons; amino; alkylamino having 1–6 carbons; dialkylamino having 2–12 carbons; carboxy; or carboxyalkyl, carboxyalkoxy, carboxyalkylamino, or carboxyalkylthio, each having 2–7 carbons;

wherein each aryl or heteroaryl is optionally and independently substituted by hydrogen, halogen; CN; alkyl, perfluoroalkyl, or alkoxy, each having 1–6 carbon atoms; carboxy; carboxyalkyl, carboxyalkoxy, carboxyalkylamino, or carboxylalkylthio, each having 2–7 carbon atoms; amino, salt of amino, alkylamino, or dialkylamino, where each alkyl group has 1–6 carbons; or an anionic moiety;

Q is a single covalent bond; or Q is a formal single bond, and $R^4$ and $R^5$ when taken in combination are $-CR^9=CR^{10}-$; or Q is $-(CR^{11}_2)_a-X_b-(CR^{12}_2)_c-$, where a, b and c are each 0 or 1; or Q is a 2,6-disubstituted pyridyl;

wherein $R^9$ and $R^{10}$ are independently H; alkyl, perfluoroalkyl, or alkoxy having 1–6 carbon atoms; a sulfonic acid, a salt of sulfonic acid; an amino, alkylamino or dialkylamino, where each alkyl group has 1–6 carbon atoms; a carboxy; or carboxyalkyl, carboxyalkoxy, carboxyalkylamino or carboxyalkylthio having 2–7 carbon atoms; an aryl or heteroaryl; halogen; CN; or an anionic moiety $R^{11}$ and $R^{12}$ are independently H or alkyl having 1–6 carbon atoms;

X is optionally O, S, $NR^{13}$, or $-CR^{14}R^{15}-$;

where $R^{13}$ is H, $C_1-C_6$ alkyl, or phenyl that is optionally further substituted one or more times in any combination by alkyl, perfluoroalkyl, or alkoxy having 1–6 carbon atoms; an anionic moiety; amino, alkylamino or dialkylamino, where each alkyl group has 1–6 carbon atoms; carboxy; carboxyalkyl, carboxyalkoxy, carboxyalkylamino or carboxyalkylthio having 2–7 carbon atoms; halogen, or CN; and $R^{14}$ and $R^{15}$ are independently H, alkyl having 1–6 carbon atoms, or an anionic moiety;

said 2,6-disubstituted pyridyl is optionally further substituted by alkyl, perfluoroalkyl, or alkoxy having 1–6 carbon atoms; sulfonic acid, salt of sulfonic acid; amino, alkylamino or dialkylamino, where each alkyl group has 1–6 carbons; carboxy; or carboxyalkyl, carboxyalkoxy, carboxyalkylamino, or carboxyalkylthio having 2–7 carbons; or halogen;

provided that said nitrogen donor ligand is substituted directly or indirectly by at least one anionic moiety that is phosphate, thiophosphate, phosphonate, carboxylate, boronate, sulfate, sulfonate, thiosulfate, and thiosulfonate, or a salt thereof;

wherein said metal complex is present in a concentration of 0.10 μM to 10 μM;

a polar organic solvent at a concentration of 5–50%; and either an acidic component at a concentration of 1%–20%, or an inorganic salt that is present at a concentration of 1–50%, or both;

and optionally further comprising buffering agents, antioxidants, metal chelators, or additional detection reagents in the same or different solutions.

36. A kit, as claimed in claim 35, wherein the polar organic solvent is an alcohol having 1–6 carbon atoms or a diol having 2–6 carbon atoms; the acidic component is phosphoric acid, acetic acid, or trichloroacetic acid; and the inorganic salt is an ammonium salt or magnesium salt.

* * * * *